US012790361B2

(12) United States Patent
Bewley Clore et al.

(10) Patent No.: US 12,790,361 B2
(45) Date of Patent: Nov. 10, 2026

(54) **ANTIBACTERIAL AND ANTIFUNGAL POLYKETIDES FROM ENVIRONMENTAL *AMYCOLATOPSIS* SPP**

(71) Applicant: The United States of America, as represented by the Secretary, Department of Health and Human Services, Bethesda, MD (US)

(72) Inventors: Carole A. Bewley Clore, Bethesda, MD (US); Hongbing Liu, Bethesda, MD (US); Shannon I. Ohlemacher, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 828 days.

(21) Appl. No.: 17/909,051

(22) PCT Filed: Mar. 16, 2021

(86) PCT No.: PCT/US2021/022571

§ 371 (c)(1), (2) Date: Sep. 2, 2022

(87) PCT Pub. No.: WO2021/188543

PCT Pub. Date: Sep. 23, 2021

(65) Prior Publication Data

US 2023/0106760 A1 Apr. 6, 2023

Related U.S. Application Data

(60) Provisional application No. 62/990,557, filed on Mar. 17, 2020.

(51) Int. Cl.

| | |
|---|---|
| ***C07H 7/02*** | (2006.01) |
| ***C12N 1/205*** | (2026.01) |
| ***C12N 9/10*** | (2006.01) |
| ***C12N 15/52*** | (2006.01) |
| ***C12P 19/02*** | (2006.01) |
| ***C12P 19/18*** | (2006.01) |
| ***C12P 19/58*** | (2006.01) |
| ***C12R 1/01*** | (2006.01) |

(52) U.S. Cl.

CPC ............... *C07H 7/02* (2013.01); *C12N 1/205* (2021.05); *C12N 9/1051* (2013.01); *C12N 15/52* (2013.01); *C12P 19/02* (2013.01); *C12P 19/18* (2013.01); *C12P 19/58* (2013.01); *C12R 2001/01* (2021.05)

(58) Field of Classification Search

CPC ........ C07H 7/02; C12N 1/205; C12N 9/1051; C12N 15/52; C12P 19/02; C12P 19/18; C12P 19/58; C12R 2001/01

USPC ........................................................... 514/23

See application file for complete search history.

(56) References Cited

FOREIGN PATENT DOCUMENTS

| | | |
|---|---|---|
| EP | 1 408 119 A1 | 4/2004 |
| WO | WO 00/28064 | 5/2000 |
| WO | WO 2005/024025 A1 | 3/2005 |

OTHER PUBLICATIONS

Huynh et al. Retinestatin, a Polyol Polyketide from a Termite Nest-Derived Streptomyces sp. J. Nat. Prod. 2024, 87, 591-599. (Year: 2024).*

An et al. Isolation and identification of rare actinomycetes in the rhizosphere of Valerian and screening of natural product. Xibei Nongye Xuebao (2016), 25(7), 1080-1086. (Year: 2016).*

An et al. Isolation and identification of rare actinomycetes in the rhizosphere of Valerian and screening of natural product. Xibei Nongye Xuebao (2016), 25(7), 1080-1086. (machine English translation) (Year: 2016).*

Liu et al. Structure and Biosynthesis of Aridomycins Reveal a Glycosylated Prodrug Strategy for Self-Resistance. J. Am. Chem. Soc. 2025, 147, 24801-24813 (Supporting Information: p. 14/55 to 55/55) (Year: 2025).*

NCBI Blast (conducted on Sep. 12, 2025): GA6-003 vs F10 or BJA-103: (Year: 2025).*

"Aflastatin A", *PubChem*, pp. 1-16 (Retrieved Aug. 31, 2022).

Berge et al., "Pharmaceutical Salts", *Journal of Pharmaceutical Sciences*, vol. 66(1): pp. 1-19 (Jan. 1, 1977).

Bolam et al., "The crystal structure of two macrolide glycosyltransferases provides a blueprint for host cell antibiotic immunity", *PNAS*, vol. 104(13): pp. 5336-5341 (Mar. 27, 2007).

Centers for Disease Control and Prevention, *Antibiotic Resistance Threats in the United States*, pp. ii-viii, 2-21 (Dec. 1, 2019).

Deluca et al., "Parenteral Drug-Delivery Systems", *Pharmaceutics and Pharmacy Practice*, pp. 238-278 (1982).

Kondo et al., "Effects of Aflastatin A, an Inhibitor of Aflatoxin Production, on Aflatoxin Biosynthetic Pathway and Glucose Metabolism in *Aspergillus parasiticus", The Journal of Antibiotics*, vol. 54(8): pp. 650-657 (Aug. 1, 2001).

*Remington's Pharmaceutical Sciences*, 18th Edition, pp. 1445 (1990).

Sakuda et al., "Blasticidin A as an Inhibitor of Aflatoxin Production by *Aspergillus parasiticus", The Journal of Antibiotics*, vol. 53(11): pp. 1265-1271 (Nov. 1, 2000).

Shimanaka et al., "Novel Antibiotics, Amythiamicins I. Taxonomy, Fermentation, Isolation, Physico-Chemical Properties, and Antimicrobial Activity", *The Journal of Antibiotics*, vol. 47(6): pp. 668-674 (Jan. 7, 1994).

(Continued)

*Primary Examiner* — Yih-Horng Shiao

(74) *Attorney, Agent, or Firm* — Leydig, Voit & Mayer, Ltd.

(57) ABSTRACT

Disclosed are compounds represented by the formula: (I), wherein R is as defined herein, and pharmaceutically acceptable salts thereof. Also disclosed are a method of treating a subject in need of treatment for a bacterial infection or a fungal infection, which includes administering to the subject an effective amount of one of the compounds or salts thereof. Further disclosed is a process for producing the compounds and salts thereof.

21 Claims, 20 Drawing Sheets

Specification includes a Sequence Listing.

(56) References Cited

OTHER PUBLICATIONS

Trissel, Lawrence A., "Intravenous Infusion Solutions", *ASHP Handbook on Injectable Drugs Fourth Edition*, pp. 622-646 (1986).
Wencewicz, Timothy A., "Crossroads of Antibiotic Resistance and Biosynthesis", *Elsevier*, pp. 1-67 (2019).
Zmudka et al., "The structure of DesR from *Streptomyces venezuelae*, a β-glucosidase involved in macrolide activation", *Protein Science 2012*, vol. 22: pp. 883-892 (Dec. 6, 2012).
European Patent Office, Written Opinion and International Search Report issued in International Application No. PCT/US2021/022571 (Oct. 12, 2021).

* cited by examiner

1

2

3

4

13C NMR

ANTIBACTERIAL AND ANTIFUNGAL POLYKETIDES FROM ENVIRONMENTAL *AMYCOLATOPSIS* SPP

CROSS-REFERENCE TO RELATED APPLICATIONS

The present application is the U.S. national phase of International Application No. PCT/US2021/022571, filed on Mar. 16, 2021, which claims the benefit of U.S. Provisional Application No. 62/990,557, filed Mar. 17, 2020, the disclosures of which are incorporated herein in their entireties for all purposes.

FEDERALLY SPONSORED RESEARCH OR DEVELOPMENT

This invention was made with Government support under project number Z01-DK031135 by the National Institutes of Health, National Institute of Diabetes and Digestive and Kidney Diseases. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 14,831 Byte ASCII (Text) file named “763538_ST25.TXT.” dated Aug. 29, 2022.

BACKGROUND OF THE INVENTION

Clinically useful antibiotics and antifungals can be separated into two classes—those agents produced naturally by microorganisms and those agents which are fully synthetic. Microorganisms have proved to be a highly significant source for production of particularly antibiotic agents as well as antifungal agents. Since the isolation of streptomycin from Streptomycetes *griseus*, various species of Streptomycetes have been explored for their production of novel antibiotic agents. Other microorganisms, such as those of the *Amycolatopsis* genus, have similarly been investigated for their production of antibiotic agents.

The *Amycolatopsis* genus has been exploited to produce many types of antibiotics, including, for example, Epoxyquinomicin, Vancomycin, and Ristocetin. Vancomycin, in particular, has found particular clinical efficacy in the treatment of various antibiotic-resistant bacterial infections.

However, the frequent use of single or multiple antibiotic agents has resulted in the emergence of resistant bacterial strains. For example, some bacteria, including *Staphylococcus aureus*, are resistant to more than 4 different antibiotic agents. This antibiotic resistance presents a significant threat to mammalian health. The threat is exacerbated by a dwindling number of antimicrobial compounds in the development pipeline. Actinomycete genomes routinely contain upwards of 20 biosynthesis gene clusters (BGCs) encoding secondary metabolites, but challenges remain in isolating novel actinomycete strains (the order to which *Amycolatopsis* belongs) from the environment and expressing the BGCs under laboratory culture conditions.

Thus, there remains in the art an urgent and unmet need for novel antibiotic agents.

BRIEF SUMMARY OF THE INVENTION

The invention provides a compound represented by the structure:

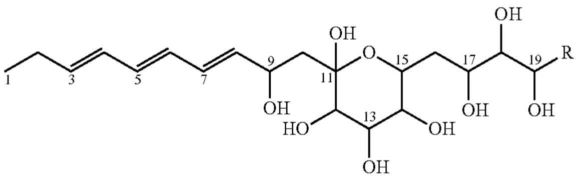

wherein R is selected from the group consisting of:

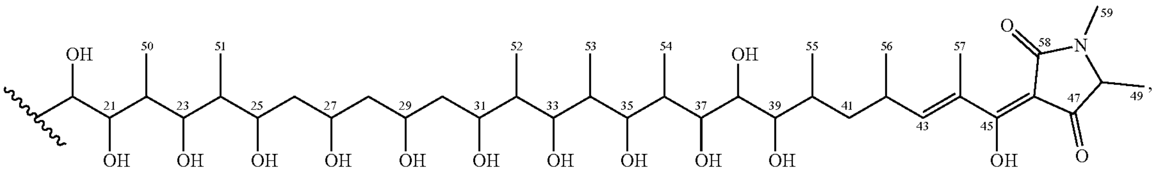

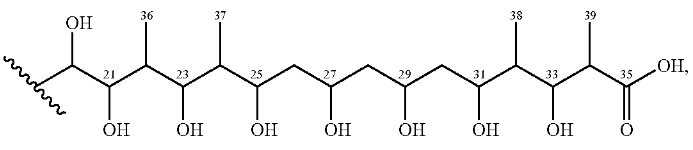

and

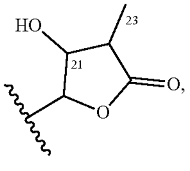

or a pharmaceutically acceptable salt thereof.

The invention also provides a method of treating a subject in need of treatment for a bacterial infection, comprising administering to the subject a therapeutically effective amount of a compound represented by the structure:

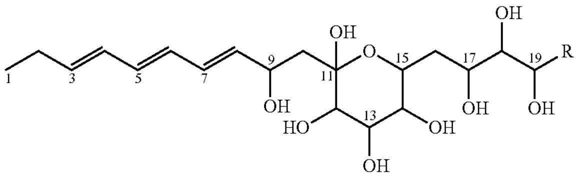

wherein R is as indicated above, or a pharmaceutically acceptable salt thereof.

The invention further provides a method of treating a subject in need of treatment for a fungal infection, comprising administering to a mammal in need thereof a therapeutically effective amount of a compound represented by the structure:

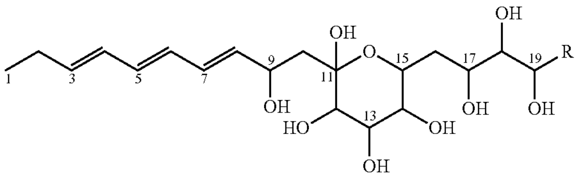

wherein R is as described above, or a pharmaceutically acceptable salt thereof.

The invention additionally provides a method for producing a compound or salt of the invention, comprising culturing a microorganism that is *Amycolatopsis* strain F10 or *Amycolatopsis* strain GA6-003 in a culture medium, thereby producing the compound or salt in an extracellular culture solution, separating the microorganism and the extracellular culture solution, and recovering the compound from the extracellular culture solution

BRIEF DESCRIPTION OF THE SEVERAL VIEWS OF THE DRAWING(S)

FIG. 18A and FIG. 18B show, respectively, the peak areas of tylosin and compound 1 and erythromycin and compound 1, as a function of time. FIG. 18C shows the peak areas of compound 1 with and without the presence of the glycosyltransferase enzyme.

Figure 19A:
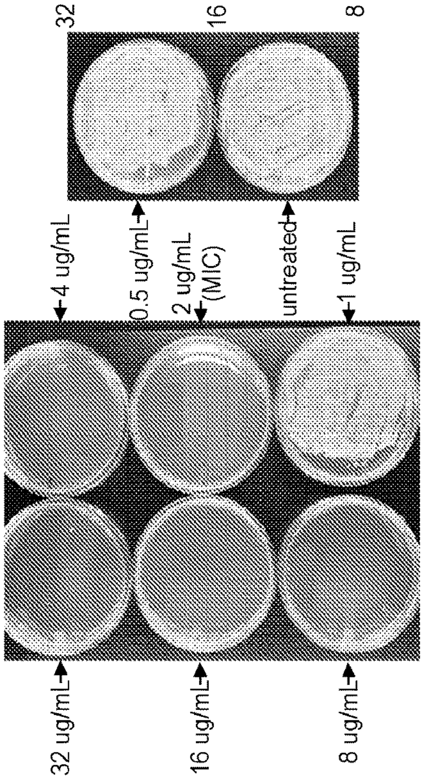
Figure 19B:
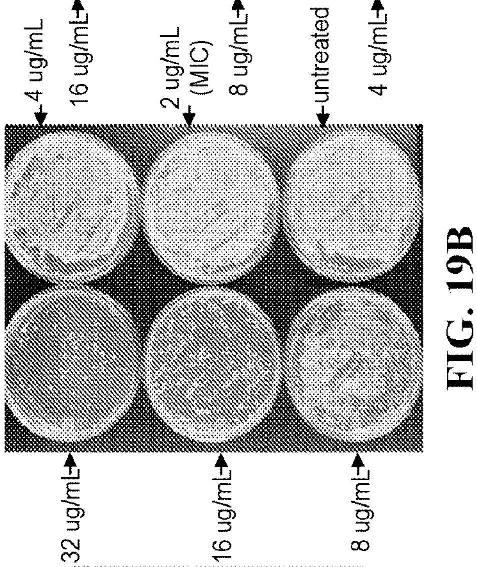
Figure 19C:
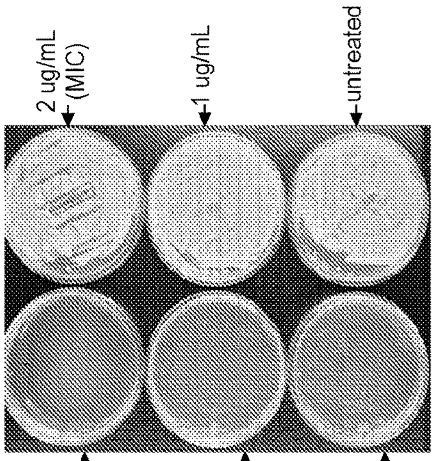

FIGS. 19A-C show the bactericidal activity of compound 2 against *S. aureus* ATCC 29213. FIG. 19A displays the activity of oxacillin, bactericidal control, MIC in the experiment=2 μg/mL. FIG. 19B displays the activity of chloramphenicol, bacteriostatic control, MIC in the experiment=8 μg/mL. FIG. 19C displays the activity of compound 2, MIC in the experiment=2 μg/mL.

Figure 20A:
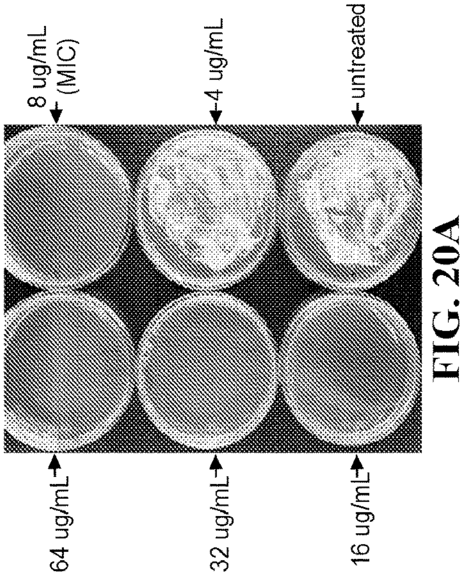
Figure 20B:
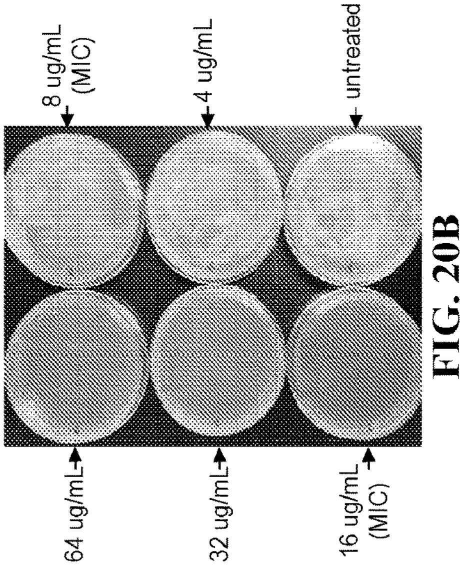

FIG. 20A-B show the fungicidal activity of compound 2. FIG. 20A displays the activity against *C. albicans* ATCC 28517, MIC in the experiment=8 μg/mL. FIG. 20B displays the activity against *C. auris* ATCC MYA-5001, MIC in the experiment=16 μg/mL.

DETAILED DESCRIPTION OF THE INVENTION

In an aspect, the invention provides a compound represented by the structure:

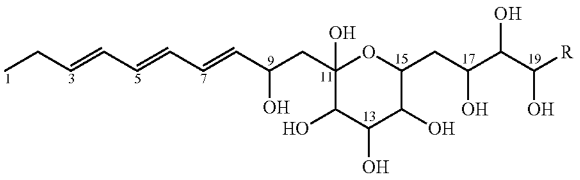

wherein R is selected from the group consisting of:

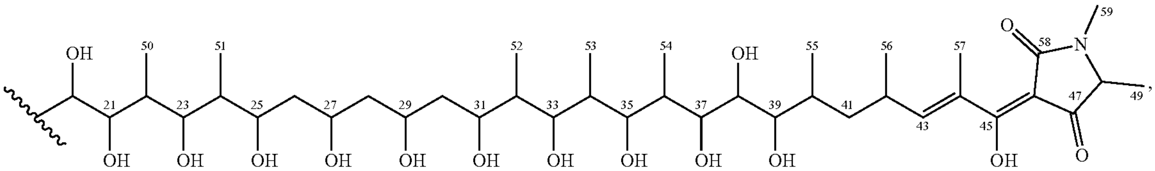

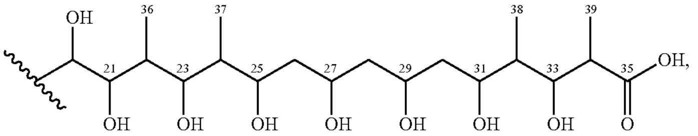

and

-continued

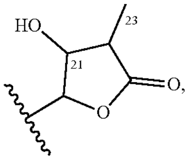

or a pharmaceutically acceptable salt thereof.

In an Aspect of the Invention, the Compound is:

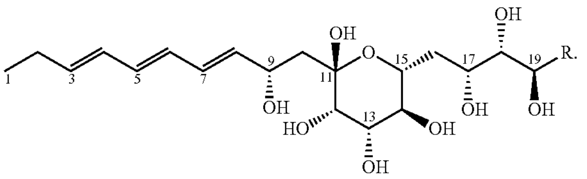

In Another Aspect of the Invention, R is:

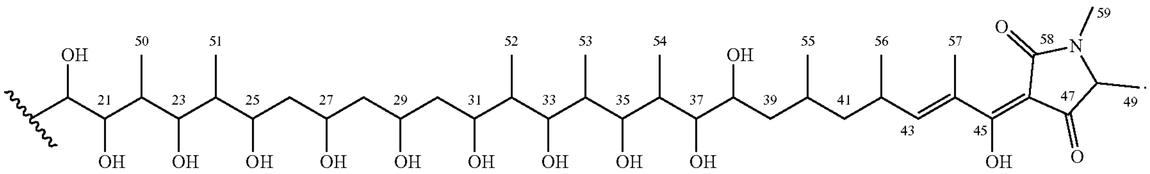 [SMILES: *C(O)C(O)C(C)C(O)C(C)C(O)CC(O)CC(O)CC(O)C(C)C(O)C(C)C(O)C(C)C(O)C(O)CC(C)CC(C)/C=C(C)/C(O)=C1/C(=O)C(C)N(C)C1=O]

In Another Aspect, R is

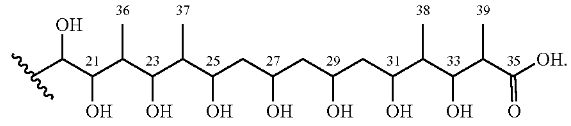 [SMILES: *C(O)C(O)C(C)C(O)C(C)C(O)CC(O)CC(O)CC(O)C(C)C(O)C(C)C(=O)O]

In a Further Aspect, R is:

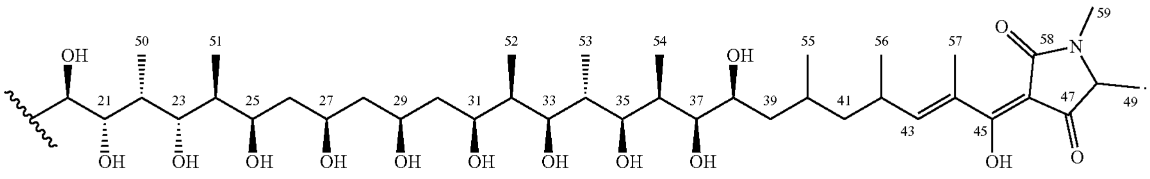 [SMILES: *[C@@H](O)[C@@H](O)[C@H](C)[C@@H](O)[C@@H](C)[C@H](O)C[C@H](O)C[C@H](O)C[C@H](O)[C@@H](C)[C@H](O)[C@H](C)[C@H](O)[C@@H](C)[C@H](O)[C@@H](O)CC(C)CC(C)/C=C(C)/C(O)=C1/C(=O)C(C)N(C)C1=O]

In any of the aspects of the compound, when a chiral carbon atom is depicted in a planar configuration, the chiral carbon atom can have any absolute configuration, e.g., the chiral carbon atom can have the R or S configuration. The inventive compounds encompass all configurations at all carbon atoms, e.g., all combinations of R and S isomers at all chiral carbon atoms. Thus, the inventive compounds encompass any single pure stereoisomer and all combinations of every possible mixtures of isomers at every single chiral carbon atoms, e.g., all combinations of diastereoisomers (i.e., diastereomers) and combinations and mixtures of diastereoisomers. When a compound is depicted as having one or more chiral carbon atoms bearing a methyl group in a planar configuration, the compound includes every combination of stereoisomers at the aforesaid chiral carbon atoms. For example, when a compound is depicted as having one chiral carbon atom in a planar configuration, the compound includes both the R and S stereoisomers at the chiral carbon atom. When a compound is depicted as having two chiral carbon atoms in a planar configuration, the compound includes all possible (R,R), (R,S), (S,R), and (S,S) combinations of stereoisomers at the chiral carbon atoms.

In another aspect, the invention provides a pharmaceutical composition represented by the structure:
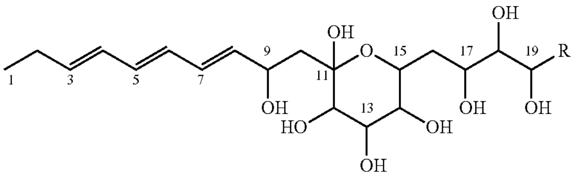
wherein R is selected from
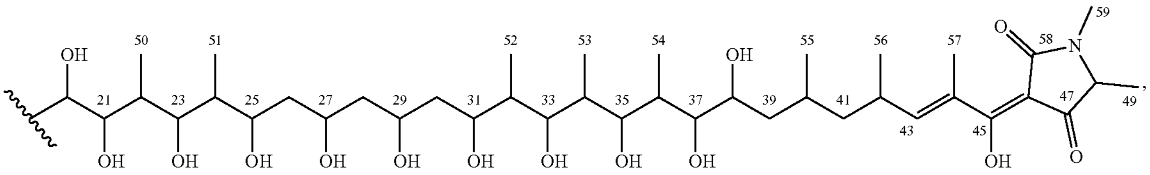
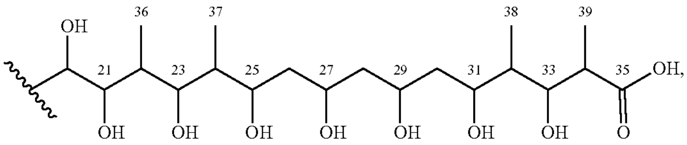
and
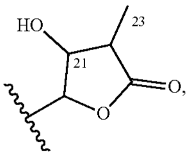
or a pharmaceutically acceptable salt thereof and a pharmaceutically acceptable carrier.
In an aspect of the pharmaceutical composition, the compound is:
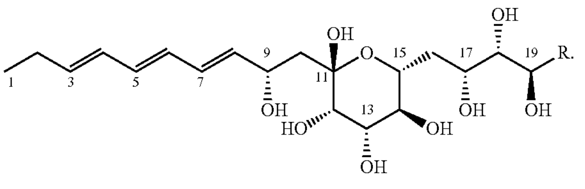
In an aspect of the pharmaceutical composition, R of the compound is:
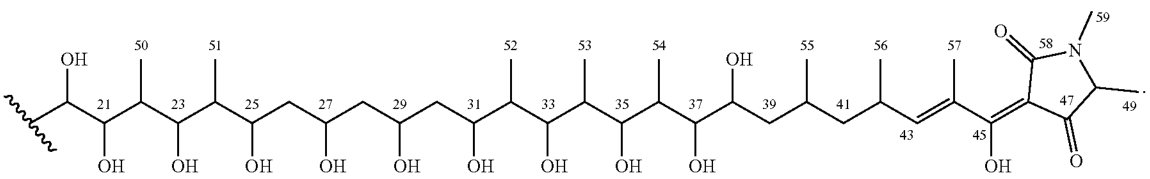 [SMILES: *C(O)C(O)C(C)C(O)C(C)C(O)CC(O)CC(O)CC(O)C(C)C(O)C(C)C(O)C(C)C(O)C(O)CC(C)CC(C)/C=C(C)/C(O)=C1/C(=O)C(C)N(C)C1=O]

In another aspect of the pharmaceutical composition, R of the compound is:

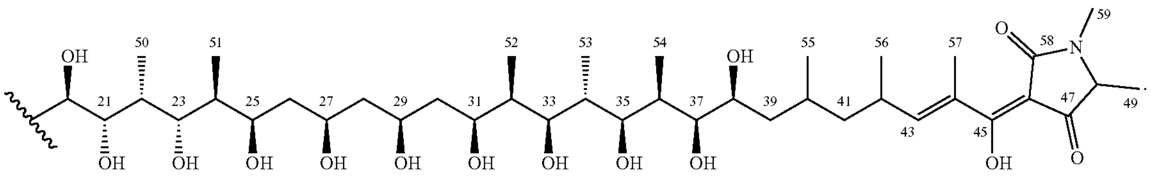 [SMILES: *[C@@H](O)[C@@H](O)[C@H](C)[C@@H](O)[C@@H](C)[C@H](O)C[C@H](O)C[C@H](O)C[C@H](O)[C@@H](C)[C@H](O)[C@H](C)[C@H](O)[C@@H](C)[C@H](O)[C@@H](O)CC(C)CC(C)/C=C(C)/C(O)=C1/C(=O)C(C)N(C)C1=O]

In another aspect of the pharmaceutical composition, R of the compound is:

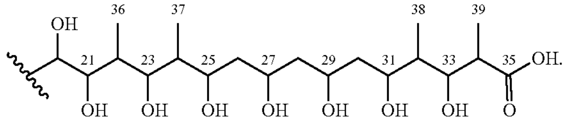 [SMILES: *C(O)C(O)C(C)C(O)C(C)C(O)CC(O)CC(O)CC(O)C(C)C(O)C(C)C(=O)O]

In another aspect, the invention provides a method of treating a subject in need of treatment for a bacterial infection, comprising administering to the subject a therapeutically effective amount of a compound represented by the structure:

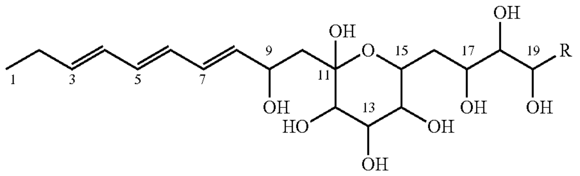

wherein R is selected from

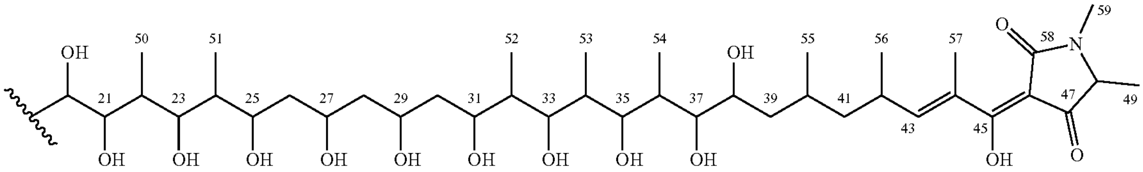

,

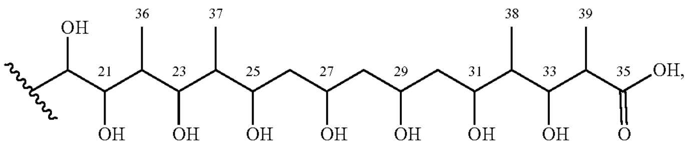

and

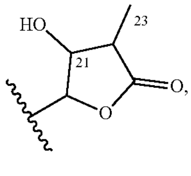

, or a pharmaceutically acceptable salt thereof.

In an Aspect of the Method, the Compound is:

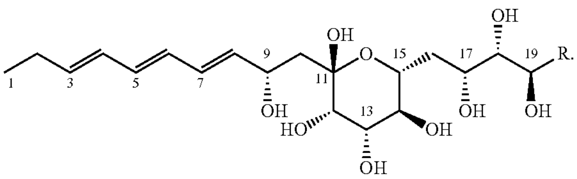

In an Aspect, R is:

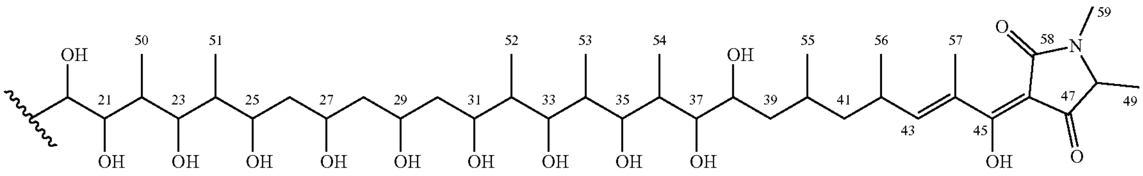

or

-continued

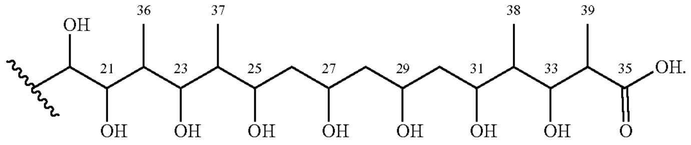

In a Further Aspect, R is:

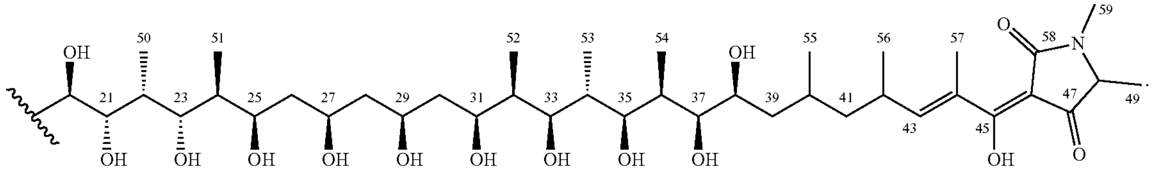 [SMILES: *[C@@H](O)[C@@H](O)[C@H](C)[C@@H](O)[C@@H](C)[C@H](O)C[C@H](O)C[C@H](O)C[C@H](O)[C@@H](C)[C@H](O)[C@H](C)[C@H](O)[C@@H](C)[C@H](O)[C@@H](O)CC(C)CC(C)/C=C(C)/C(O)=C1/C(=O)C(C)N(C)C1=O]

The bacteria causing the infection can be any bacteria that is inhibited by treatment with the inventive compounds. In certain aspects, the bacteria causing the infection are Gram-positive bacteria.

In certain particular aspects, the bacteria causing the infection are *S. aureus*, Methicillin-resistant *Staphylococcus aureus* (MRSA), *E. faecalis*, or Vancomycin-resistant *E. faecalis.*

In another aspect, the invention provides a method of treating a subject in need of treatment for a fungal infection, comprising administering to a mammal in need thereof a therapeutically effective amount of a compound represented by the structure:

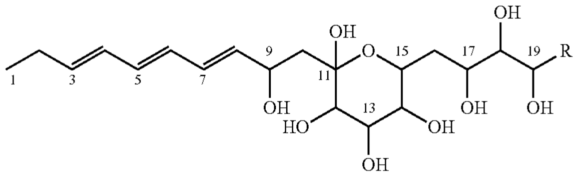

wherein R is selected from

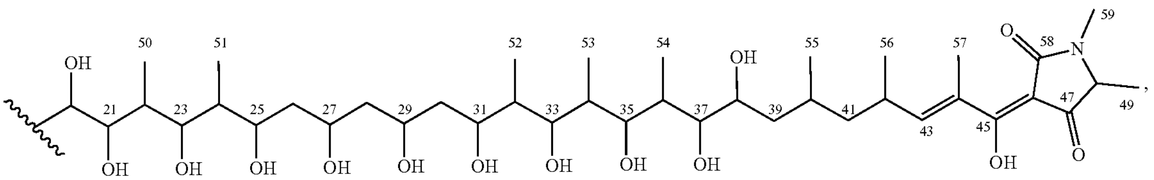

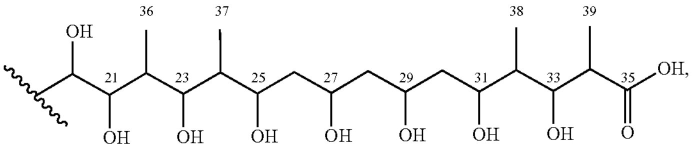

and

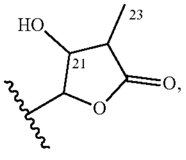

or a pharmaceutically acceptable salt thereof.

In an Aspect of the Method, the Compound is:

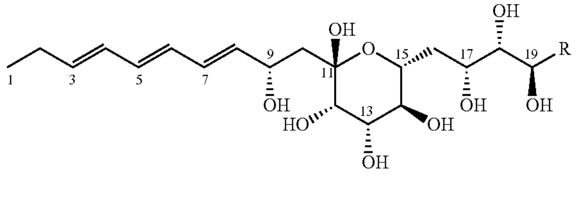

wherein R is as defined above.

In a Preferred Aspect, R is:

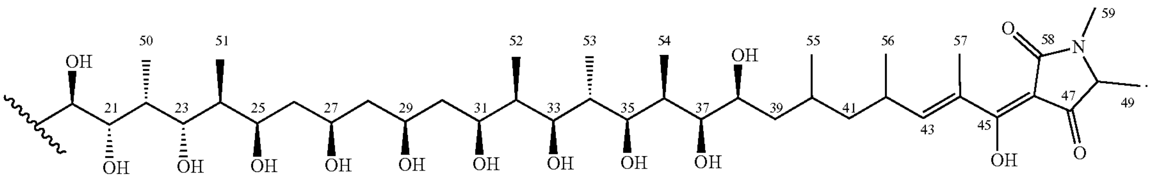

Figure 13:
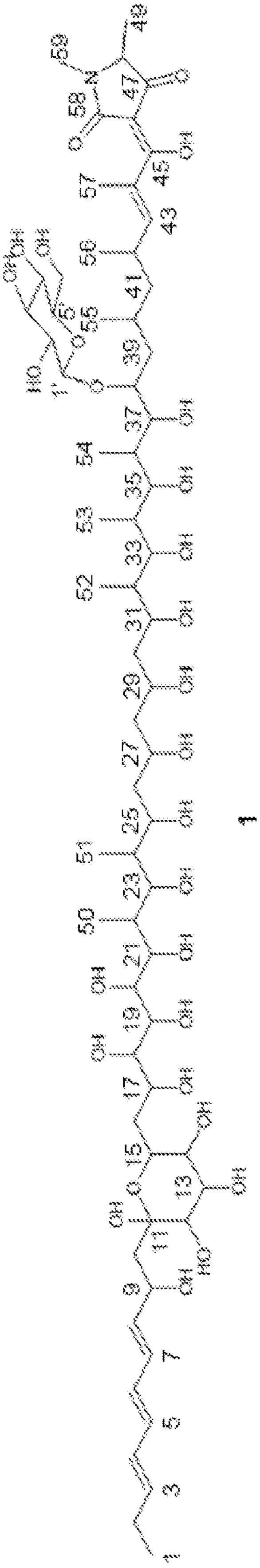
FIG. 13 shows the carbon numbering for compounds 1-3.
Figure 13:
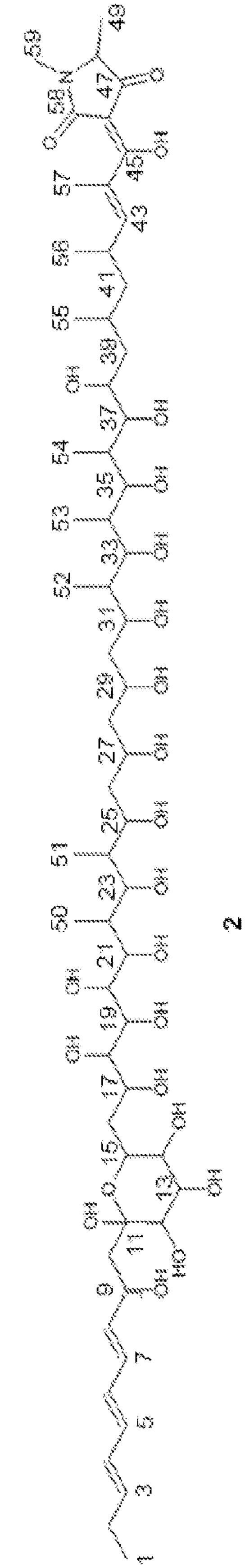
Figure 13:
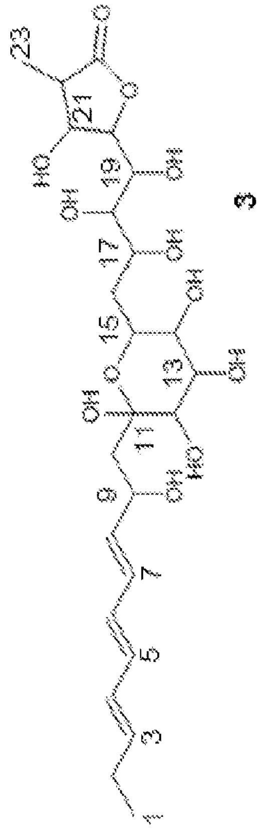
Figure 14:
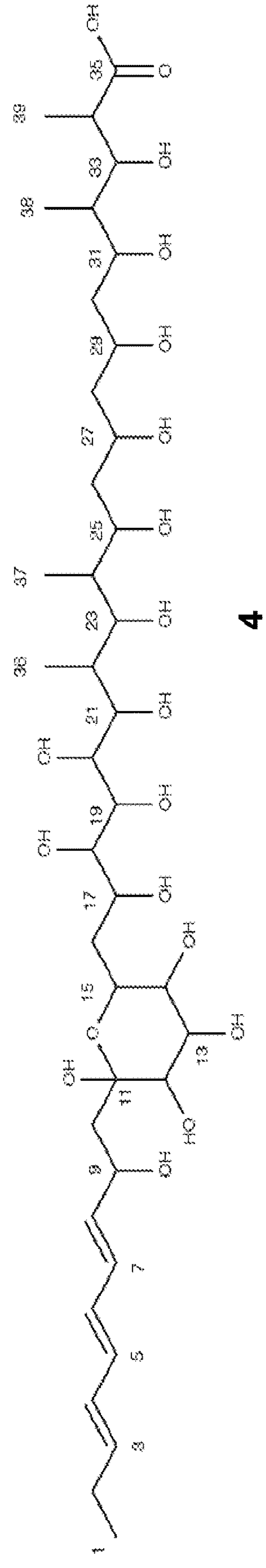
FIG. 14 shows a mass spectrum of compound 4.
Figure 15:
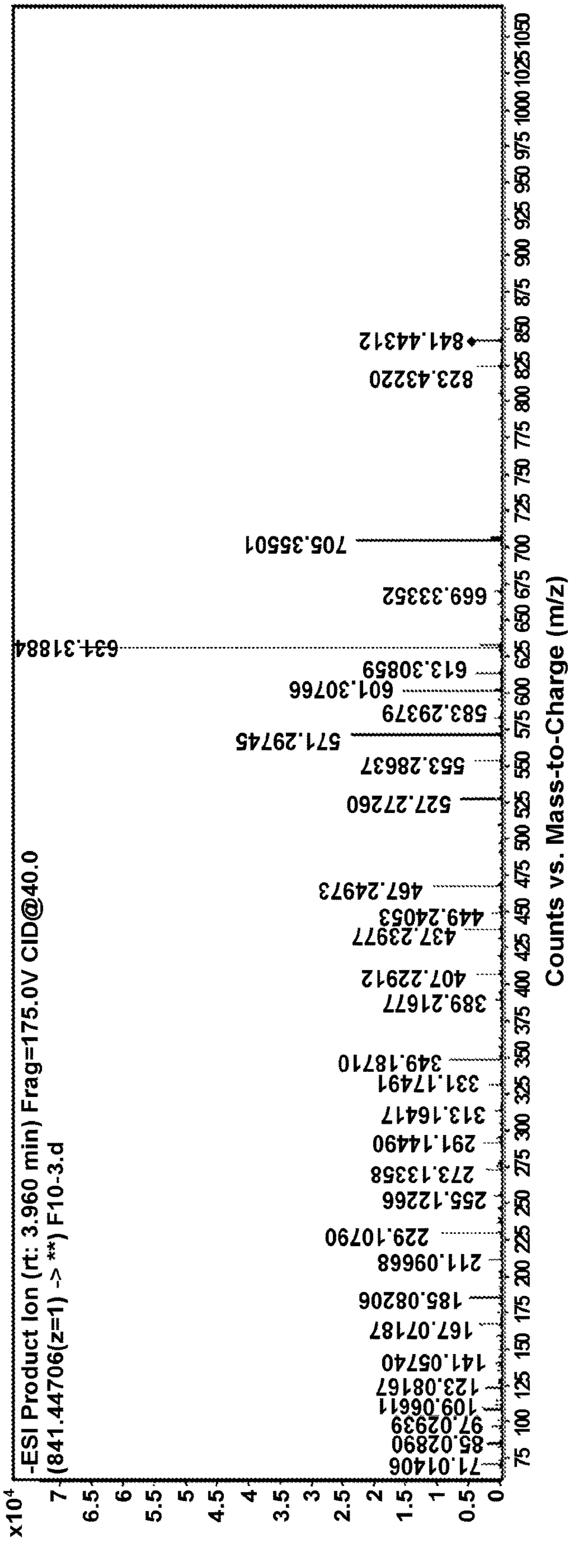
FIG. 15 shows a $^{1}$H-NMR spectrum of compound 4.
Figure 16:
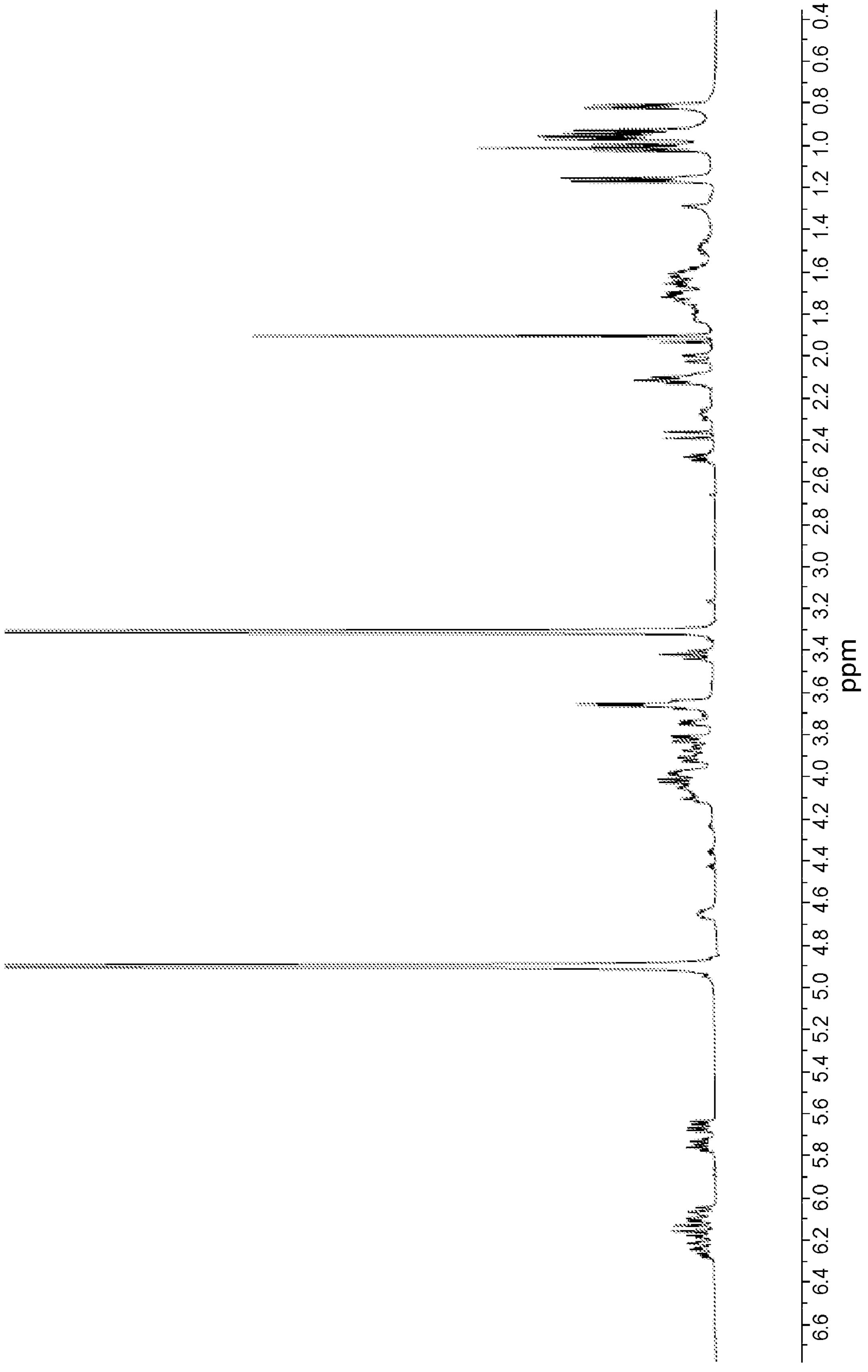
FIG. 16 shows a $^{13}$C-NMR spectrum of compound 4.
Figure 17:
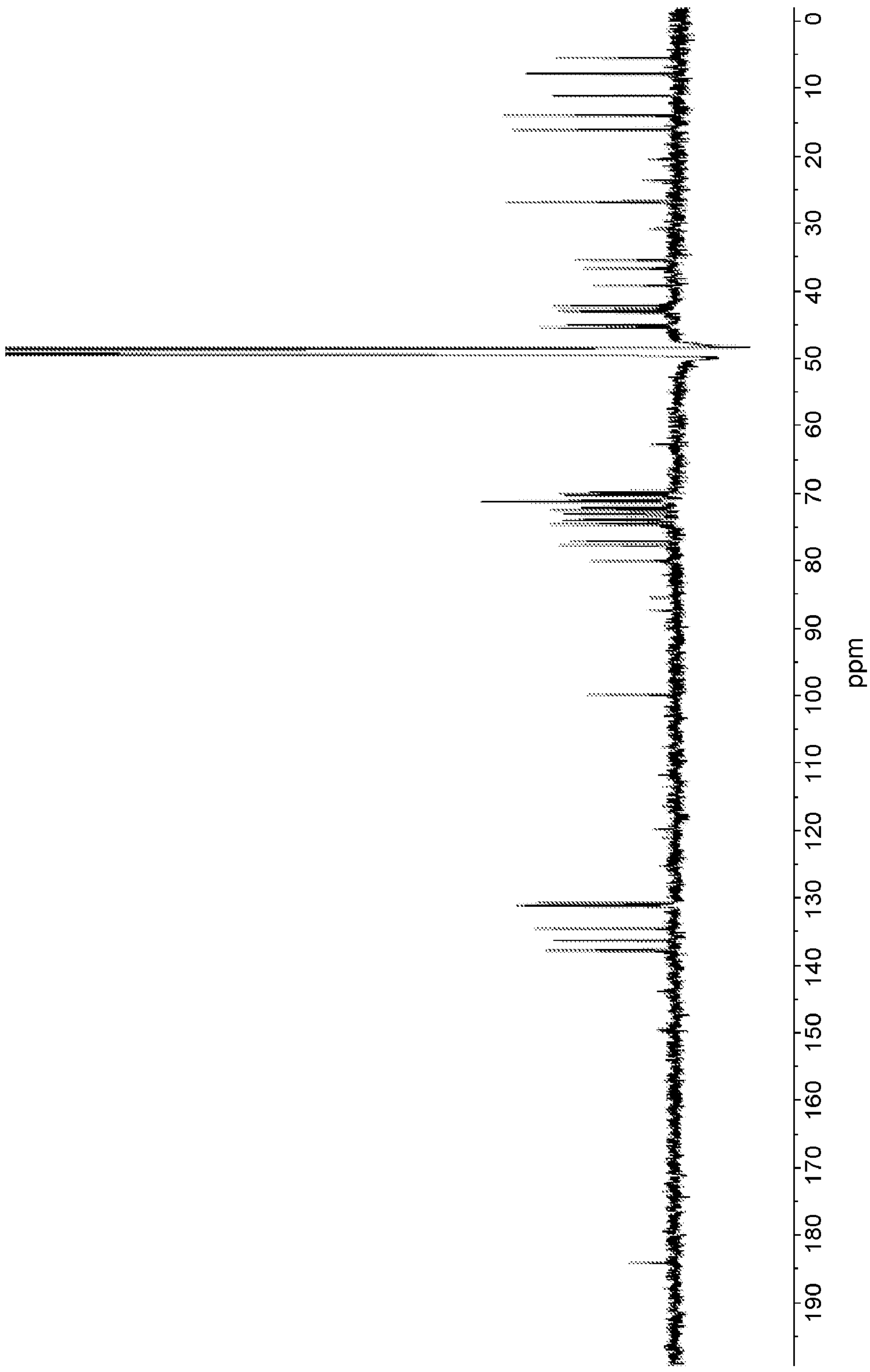
FIG. 17 shows the structure of compound 4.

Examples of suitable compounds include compounds 1-4, as set forth in FIGS. 13 and 14.

The fungus causing the infection can be any fungus that is inhibited by treatment with the inventive compounds. In certain particular aspects, the fungus causing the infection is *C. albicans* or Amphotericin B-resistant *C. albicans.*

In any of the above aspects, the subject is a mammal.

The present invention also provides a compound or salt as described above for use in the treatment of a subject in need of treatment of a bacterial infection or a fungal infection or for use in the prevention of a bacterial infection or a fungal infection.

In another aspect, the invention provides a method for treating or prevention of pathologies associated with microbial infection, particular bacterial or fungal infection. In some aspects, non-limiting examples of pathologies associated with microbial infection include sepsis, septicaemia, nosocomial disease, including *Staphylococcus aureus* infection, cellulitis, osteomyelitis, syphilis, meningitis, cystitis, pyelonephritis, and candidiasis (e.g., thrush and vaginal yeast infections).

The phrase "pharmaceutically acceptable salt" is intended to include nontoxic salts synthesized from the parent compound which contains an acidic moiety by conventional chemical methods. Generally, such salts can be prepared by reacting the free acid forms of these compounds with a stoichiometric amount of the appropriate acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, PA, 1990, p. 1445, and *Journal of Pharmaceutical Science,* 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Preferred pharmaceutically acceptable salts of inventive compounds having an acidic moiety (i.e., the tetramic acid moiety) include sodium and potassium salts. The compounds of the present invention containing an acidic moiety are useful in the form of the free acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as ethanolates, acetonitriles, and the like. These compounds can also exist in polymorphic forms.

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some aspects, the composition contains at least one active component and a suitable vehicle or carrier. It may also contain other components, such as an anti-irritant. The carrier can be a liquid, solid or semi-solid. In aspects, the composition is an aqueous solution. Alternatively, the composition can be a dispersion, emulsion, gel, lotion or cream vehicle for the various components. In one aspect, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In aspects of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The compounds or salts thereof can be used in any suitable dose. Suitable doses and dosage regimens can be determined by conventional range finding techniques. Generally, treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. The dosages range from about 0.001 to about 1000 mg/kg body weight of the animal being treated/day. For example, in certain aspects, the compounds or salts may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

The invention also provides a method for producing a compound represented by the structure:

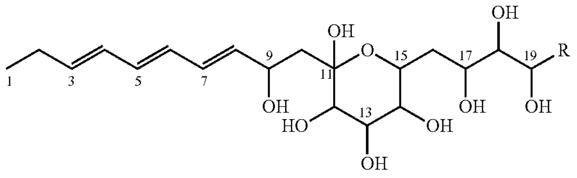

wherein R is selected from

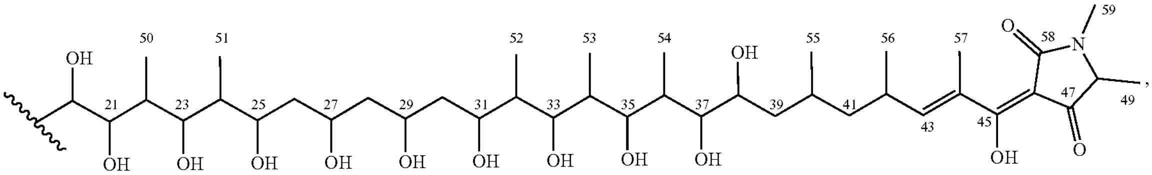

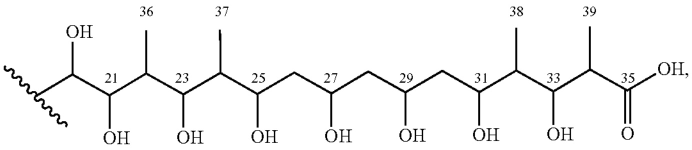

and

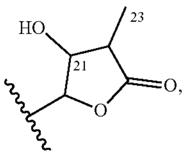

or a pharmaceutically acceptable salt thereof, comprising culturing a microorganism that is *Amycolatopsis* strain F10 or *Amycolatopsis* strain GA6-003 in a culture medium, thereby producing the compound in an extracellular culture solution, separating the microorganism and the extracellular culture solution, and recovering the compound from the extracellular culture solution.

In an Aspect of the Method, the Compound is:

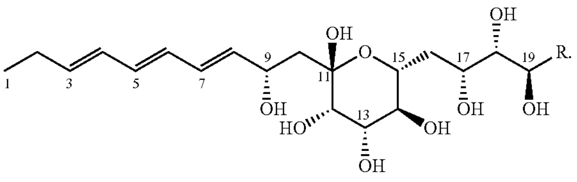

In an Aspect, R is:

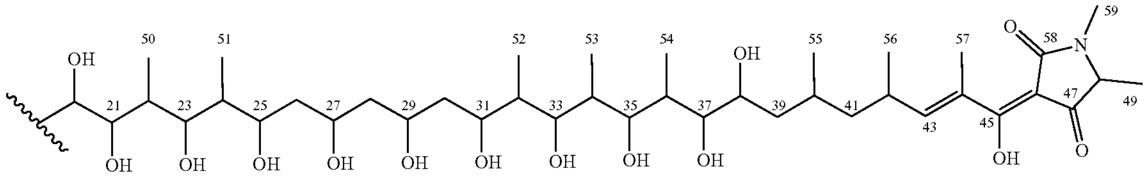

or

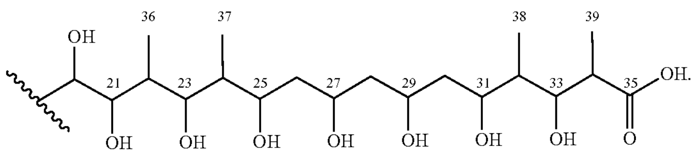

In Another Aspect, R is:

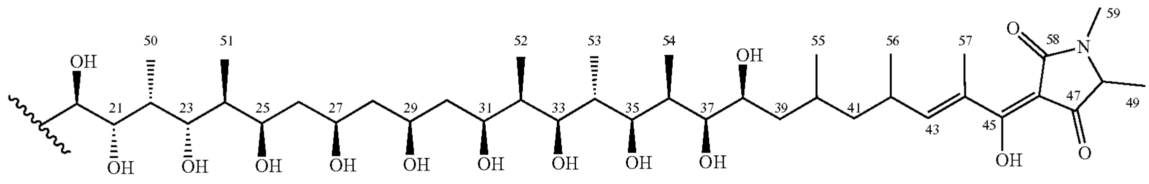

*Amycolatopsis* strain F10 or *Amycolatopsis* strain GA6-003 can be obtained from soil samples. Neither of the two *Amycolatopsis* strains express the inventive compounds in nature. In an aspect of a method of producing the compounds, a soil sample can be suspended in sterile water and serial dilutions can be plated onto, for example, solid agar media supplemented with antifungal agents, for example, cycloheximide, and/or nystatin to inhibit fungal growth and antibiotics, for example vancomycin and/or streptomycin to inhibit growth of undesired bacterial species. Following incubation, colonies can be isolated by restreaking onto agar media.

The culture medium can be any suitable culture medium in which *Amycolatopsis* strain F10 or *Amycolatopsis* strain GA6-003 expresses the inventive compounds. In some aspects, the culture medium comprises sucrose, potassium sulfate, magnesium chloride, glucose, yeast extract, and casamino acid. In some other aspects, the culture medium comprises yeast extract, beef extract, a peptone derived from casein, glucose, and agar.

In any of these aspects, the microorganism comprises a 16S ribosomal DNA having SEQ ID NO: 1 or SEQ ID NO: 2.

Separation of the microorganism from the extracellular culture solution can be performed using any suitable separation method, for example, by centrifugation. Isolation of the inventive compounds can be performed using any suitable method, many of which are known in the art. In some aspects, the extracellular culture medium is fractionated on a high pressure liquid chromatography (HPLC) column and then eluted from the column by passage of a solvent or mixture of solvents through the column. Further processing of the isolated compounds to provide a suitable physical form to formulation and storage can be performed, for example, via lyophilization of an aqueous solution of suspension of the compounds.

The following examples further illustrate the invention but, of course, should not be construed as in any way limiting its scope.

Example 1

This example demonstrates a method for production and isolation of compounds 1-4 from two strains of *Amycolatopsis* spp., referred to as F10 and GA6-003.

Two separate strains of *Amycolatopsis* sp. were isolated from California and Arizona soil samples using standard actinomycete isolation methods. 1 g of soil was suspended in 10 mL of sterile water and 100 microliters of 10-fold serial dilutions, starting at 10- and going to a 1000-fold dilution were plated onto solid agar media such as ISP2 or Asparagine media supplemented with 20 micrograms/mL vancomycin, or 25 micrograms/mL streptomycin, and 50 microgram/mL cycloheximide and 25 micrograms/mL nystatin to inhibit fungal growth. Plates were incubated at 25° C. for at least 28 days. Colonies were isolated by restreaking onto the same media using sterile techniques. Strains were archived by growing axenic isolates in liquid ISP2 media and combined with 30% glycerol final v/v followed by flash freezing at −80° C. The producing strains were identified as *Amycolatopsis* sp. based on their 16S rDNA sequences (SEQ ID NO: 1).

Table 1 sets forth the composition of the media used for the production of the compounds.

TABLE 1

| Arginine agar | ISP2 | R2YE |
|---|---|---|
| 0.30 g L-Arginine | 5.0 g Peptone | 103.0 g sucrose |
| 1.00 g Dextrose | 3.0 g Yeast extract | 0.2 g potassium sulfate |
| 1.00 g Glycerol | 3.0 g Malt extract | 10.0 g magnesium chloride |
| 0.50 g Yeast extract | 10.0 g Dextrose | 10.0 g glucose, |
| 0.30 g $K_2HPO_4$ | | 5.0 g yeast extract |
| 0.20 g $MgSO_4•7H_2O$ | | 0.1 g Difco casamino acid |
| 0.01 g $Fe_2(SO_4)3$ | | |
| 750 ml ASW | | |
| 250 ml Distilled water | | |
| 20.0 g Agar | | |
| pH. 7.3 | pH 7.2 ± 0.2 | pH 7.2 ± 0.2 |

ASW: artificial sea water

Compounds 1~4 can be produced using the following protocols.

Figure 1:
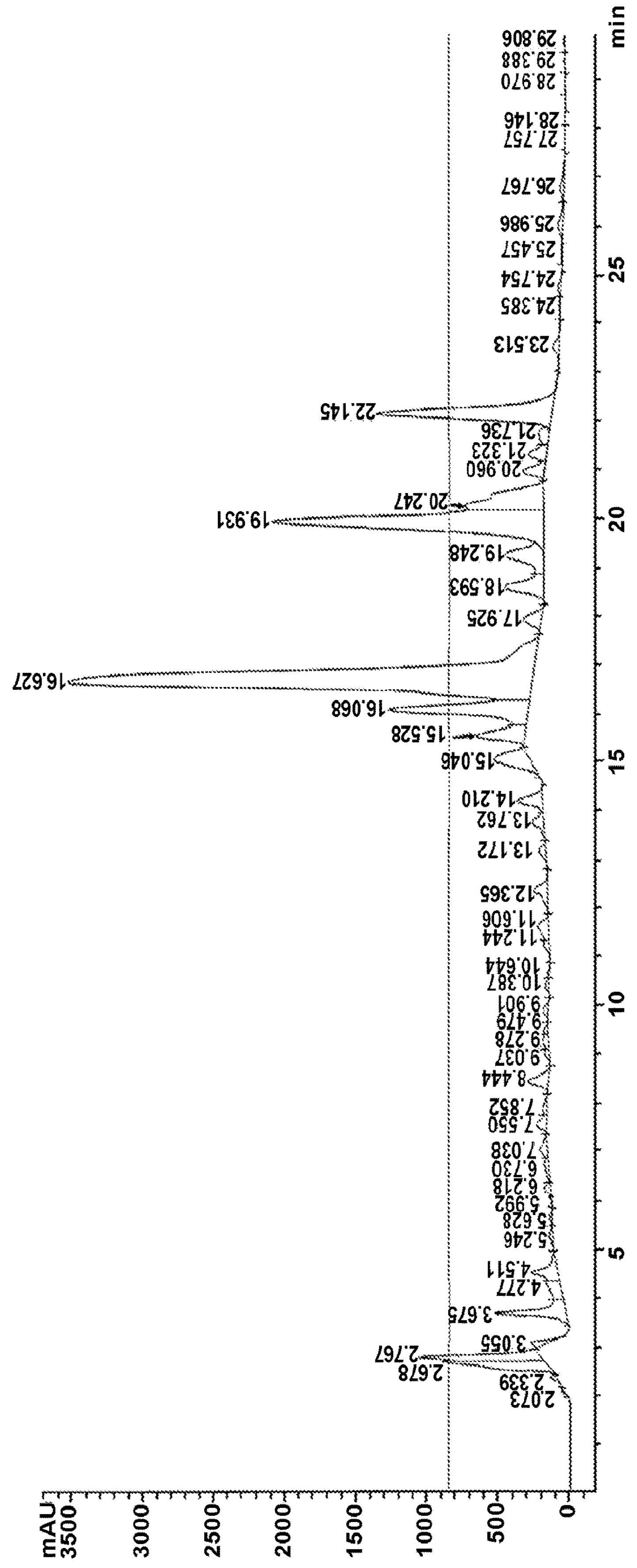
FIG. 1 shows a representative HPLC UV-detected chromatogram of the fraction eluted with 100% MeOH.

R2YE cultures: Four 1 L volumes (grown in 2 L shake flasks) of culture grown in R2YE media (containing 103 g sucrose, 10 g glucose, 5 g yeast extract, 0.2 g potassium sulfate, 10 g magnesium chloride, 0.1 g Difco casamino acid, per liter of deionized water, see Table 1) were inoculated with a single colony of *Amycolatopsis* sp. F10. Cultures were grown for 7-8 days with shaking at 200 RPM, 30° C. The culture media and cells were harvested by centrifugation at 6000 rpm at 4° C. The supernatant was chromatographed on an HP20SS-gel (Sigma-Aldrich) column equilibrated in $H_2O$ and eluted sequentially with 1 L $H_2O$, 1 L 60% MeOH, and 1 L 100% MeOH. The fraction that eluted with 100% MeOH (ca. 190 mg) was purified by semi-preparative HPLC on a Waters SymmetryPrep™ C18 column (7 micron, 7.8×300 mm). Compounds were chromatographed using a 3 mL/min flowrate, eluting with a gradient of 20-40% MeCN in 10 mM ammonium acetate in $H_2O$. Representative yields of the compounds (per 4 L, retention time $t_R$, per 1 L) are: 1 (13.3 mg, $t_R$ 16.3 min; 3.3 mg/L), 2 (3.6 mg, $t_R$ 22.2 min; 0.9 mg/L), 3 (5.2 mg, $t_R$ 20.0 min; 1.3 mg/L), and 4 ($t_R$ 8.5 min). A representative HPLC UV-detected chromatogram of the fraction eluted with 100% MeOH is shown in FIG. 1. The yield of compounds 1~4 depends on the harvest time of the culture.

Figure 2:
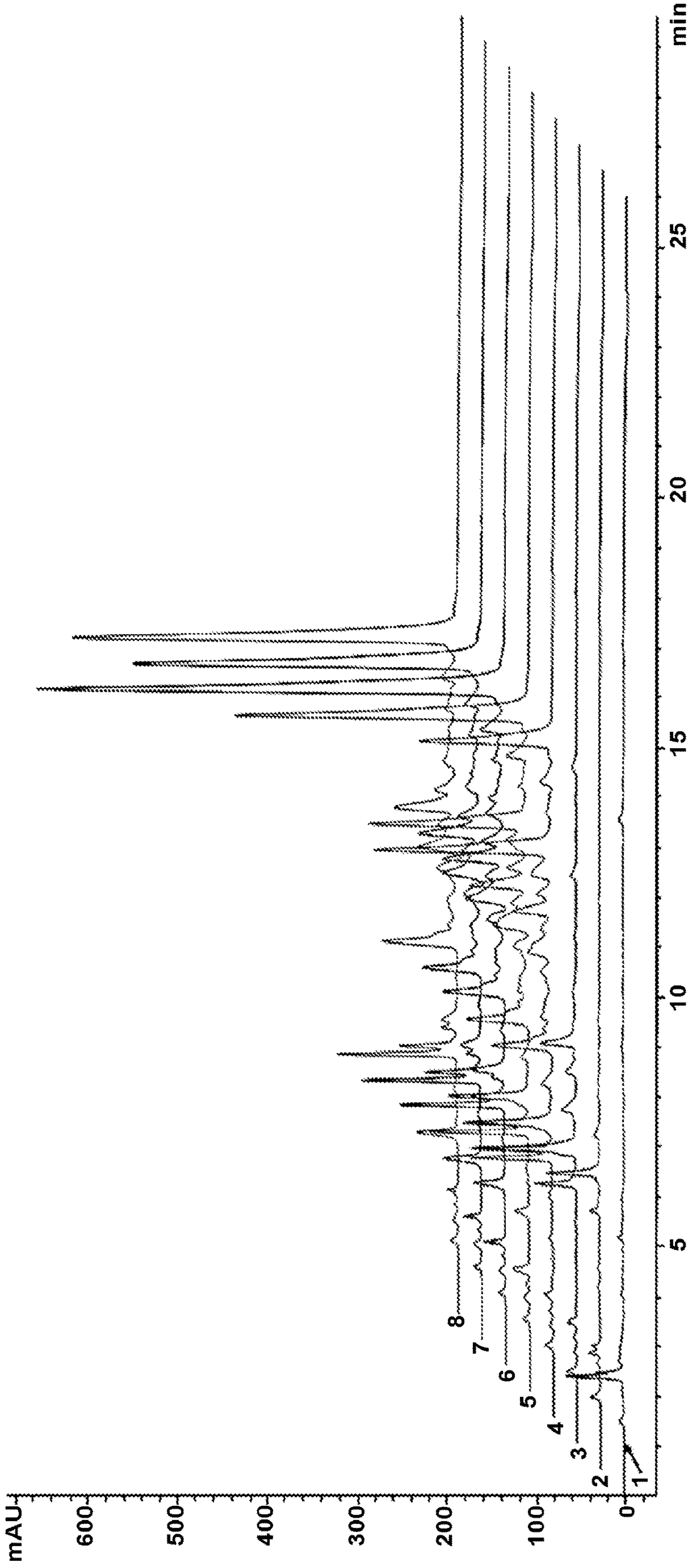
FIG. 2 shows superposed HPLC UV-detected chromatograms obtained at successive time points showing the compounds produced by *Amycolatopsis* sp. F10 during a 10-day culture.

A time course of compound production in R2YE media was carried out as follows. A single colony was inoculated into 50 mL of R2YE media and grown at 30° C. with shaking at 200 rpm. On days 3 to 10, 500 microL aliquots of the culture broth were extracted with n-butanol and 20 microliters of the n-butanol fraction were injected onto an analytical HPLC-MS system (0.8 mL/min, 0-20 min, 5-100%; 20-25 min 100-5%; MeCN—$H_2O$ gradient elution; $H_2O$ containing 0.1% formic acid) using a Waters Symmetry™ C18 5 micron, 4.6×150 mm column. The retention times of compound 1-4 are 12.0, 13.5, 10.1, and 9.3 min, respectively. Superposed HPLC UV-detected chromatograms obtained at successive time points showing the compounds produced by *Amycolatopsis* sp. F10 during a 10-day culture are shown in FIG. 2. The peak eluting at 15 min corresponds to compound 1.

Example 2

This example demonstrates a method of preparation of enriched $^{13}C$-labeled samples of compounds 1 and 2.

A 5 mL seed culture of *Amycolatopsis* sp. F10 was used to inoculate 100 mL of $^{13}C$-enriched R2YE media (10 g $^{13}C$-glucose/L). After 7 days, the seed culture was transferred into 1 L of $^{13}C$-enriched R2YE media (10 g $^{13}C$-glucose/L) and shaken at 200 RPM, 30° C. After 3 days, the culture was centrifuged at 6000 rpm and the supernatant was chromatographed on HP20SS-gel column, which was washed with water, 20% methanol, 60% methanol, and 100% methanol. The 100% methanol extract (72.8 mg) was purified by HPLC to obtain $^{13}C$-enriched compound 1 (5.3 mg) and compound 2 (2.1 mg). These samples were used to record $^{13}C$-$^{13}C$ NMR correlation spectra ($^{13}C$ COSY) to confirm the planar structures of compounds 1 and 2.

Example 3

This example demonstrates a method for purifying compound 1 from *Amycolatopsis* sp. GA6-003 in Bennett's media.

Figure 3:
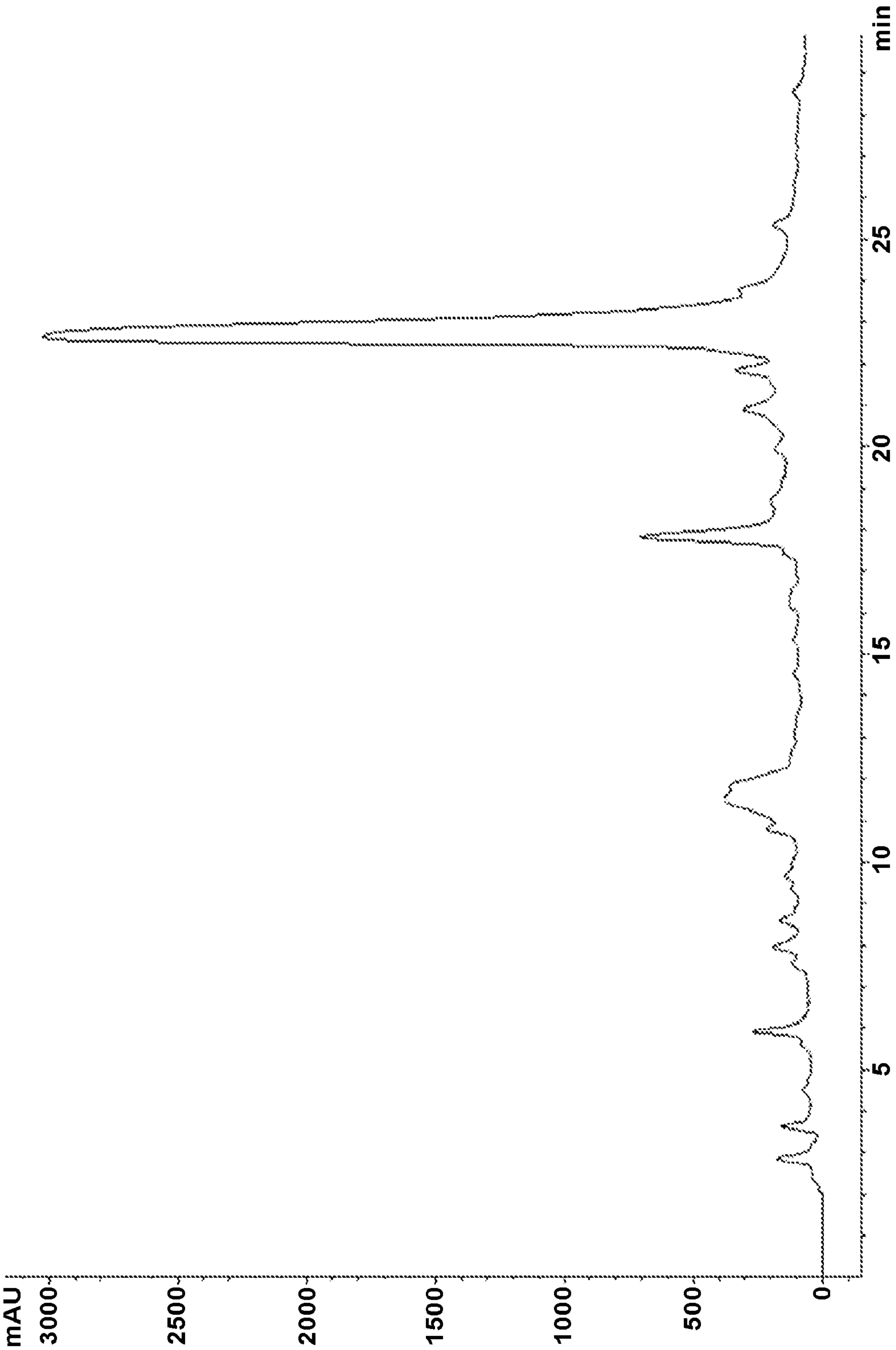
FIG. 3 shows a representative HPLC chromatogram with UV detection at 254 nm of strain GA6-003 grown in Bennett's medium.

Bennett's medium (0.5 L) in a 2.5 L Ultra Yield flask was inoculated 1:100 (v/v) with a 3-day culture of GA6-003 grown in ISP2. The culture was grown in an orbital shaking incubator for 9 days at 30° C. and 300 rpm. The culture supernatant was separated from the cells by centrifugation and loaded onto an HP20SS column. Compound 2 was eluted from the column with methanol and further purified by HPLC on a SymmetryPrep™ C18 7 μm 7.8×300 mm column using the same gradient as described above. Fractions containing compound 2, 1193 are lyophilized to remove solvent. The typical yield of compound 2 from this method was 5 mg per 1 L culture. Unlike growth in R2YE, compound 1 was not produced in quantity in this medium. A representative HPLC chromatogram with UV detection at 254 nm of strain GA6-003 grown in Bennett's medium is shown in FIG. 3. Compound 1 eluted at 22.7 min and compound 2 was not present.

Example 4

This example demonstrates the time course of production of compounds 1 and 2 by *Amycolatopsis* sp. GA6-003 and F10 grown in R2YE media.

Figure 4A:
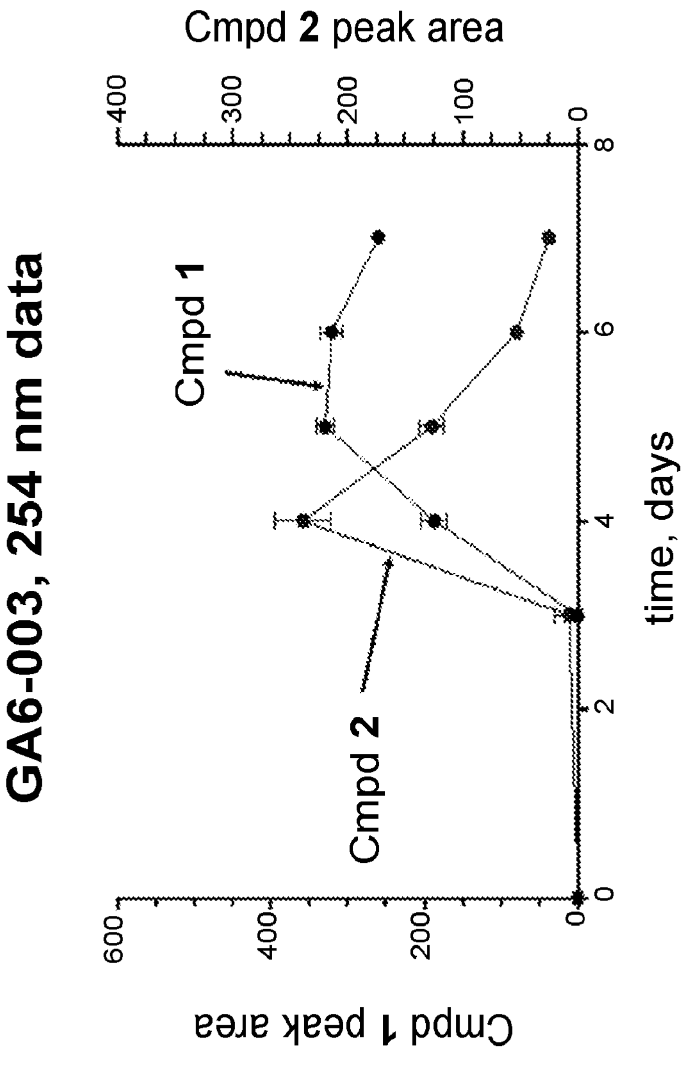
FIGS. 4A and 4B shows quantitation of compound 1 and compound 2 by HPLC at 254 nm for both GA6-003 (FIG. 4A) and F10 strains (FIG. 4B).
Figure 4B:
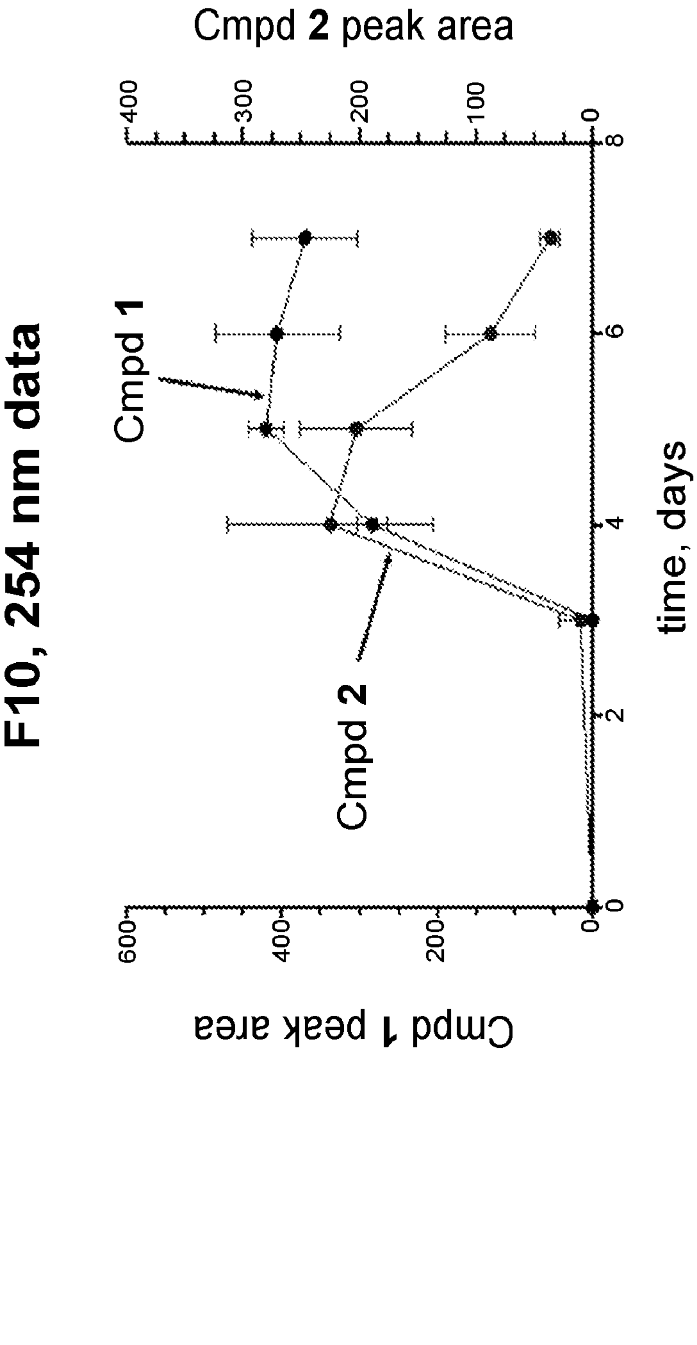
Figure 5:
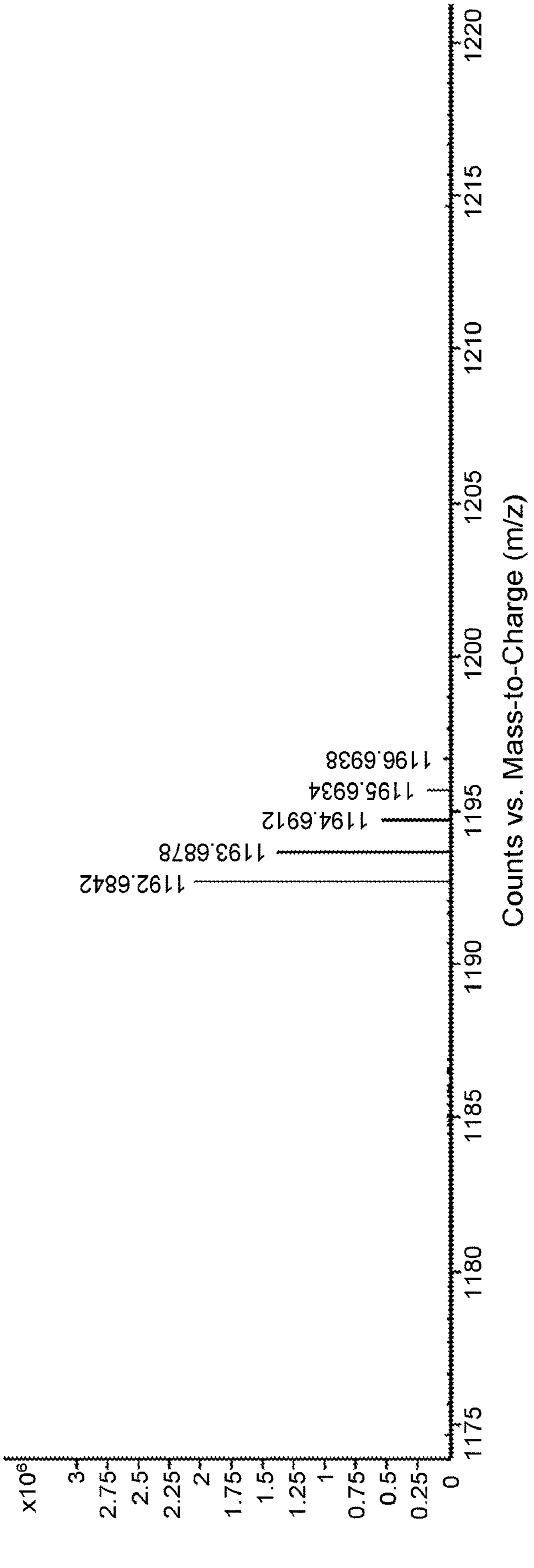
FIG. 5 shows a high resolution mass spectrum of compound 1.
Figure 6:
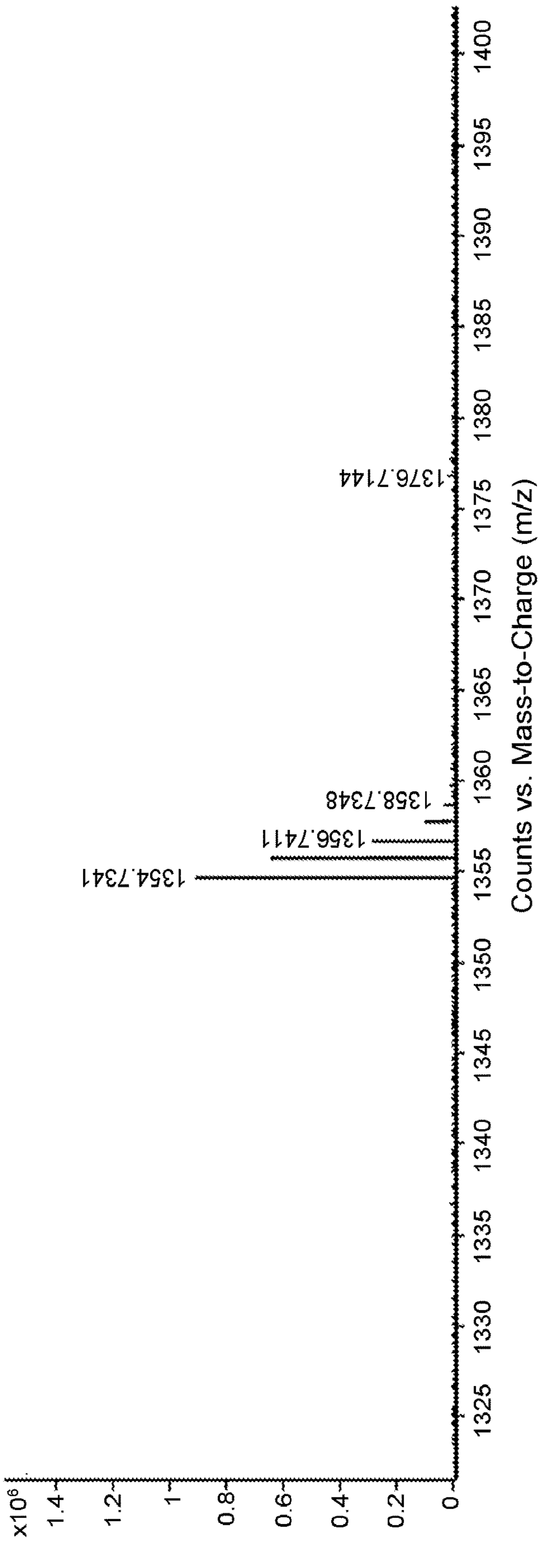
FIG. 6 shows a high resolution mass spectrum of compound 2.
Figure 7:
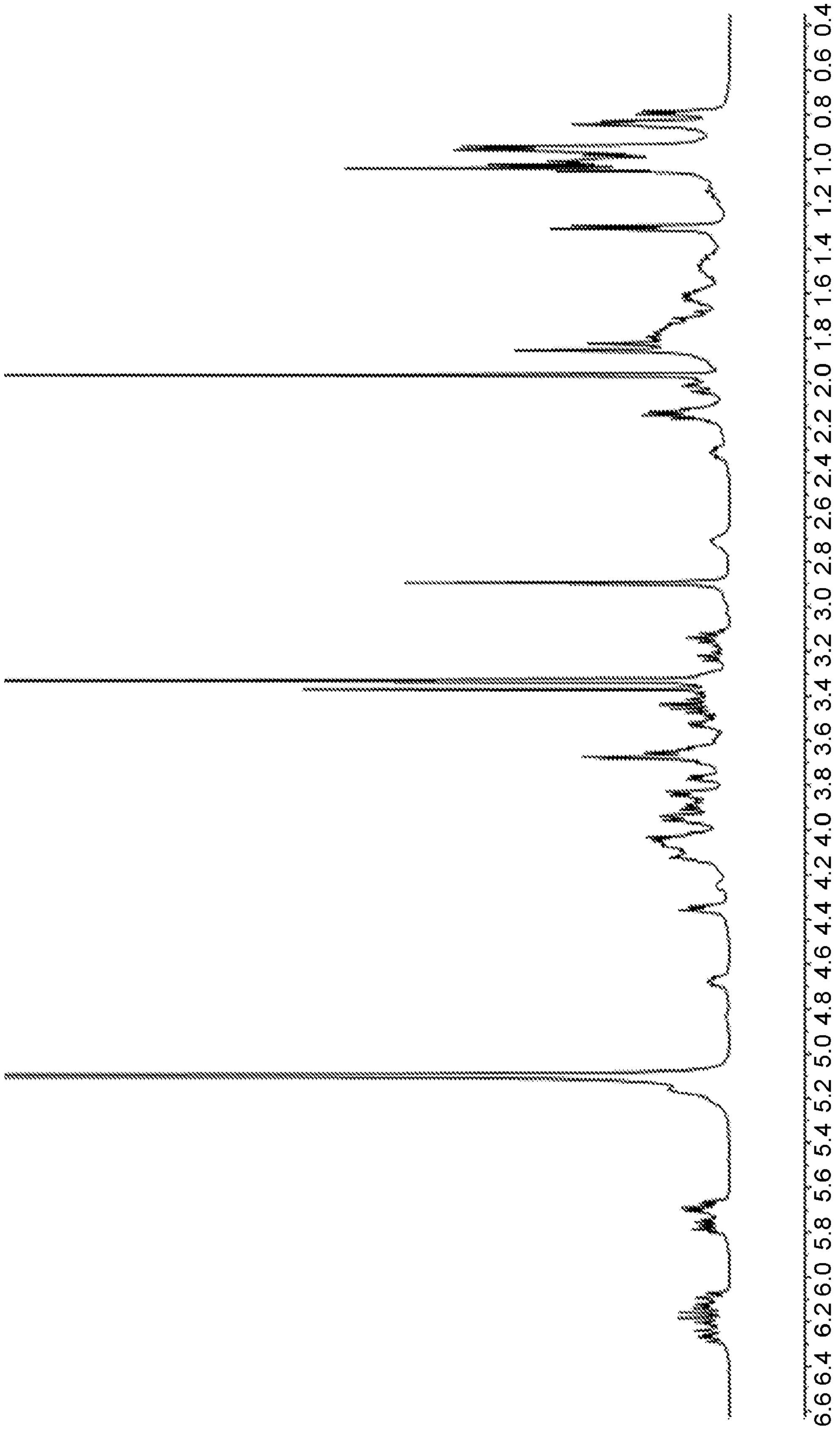
FIG. 7 shows a $^{1}$H-NMR spectrum of compound 1.
Figure 8:
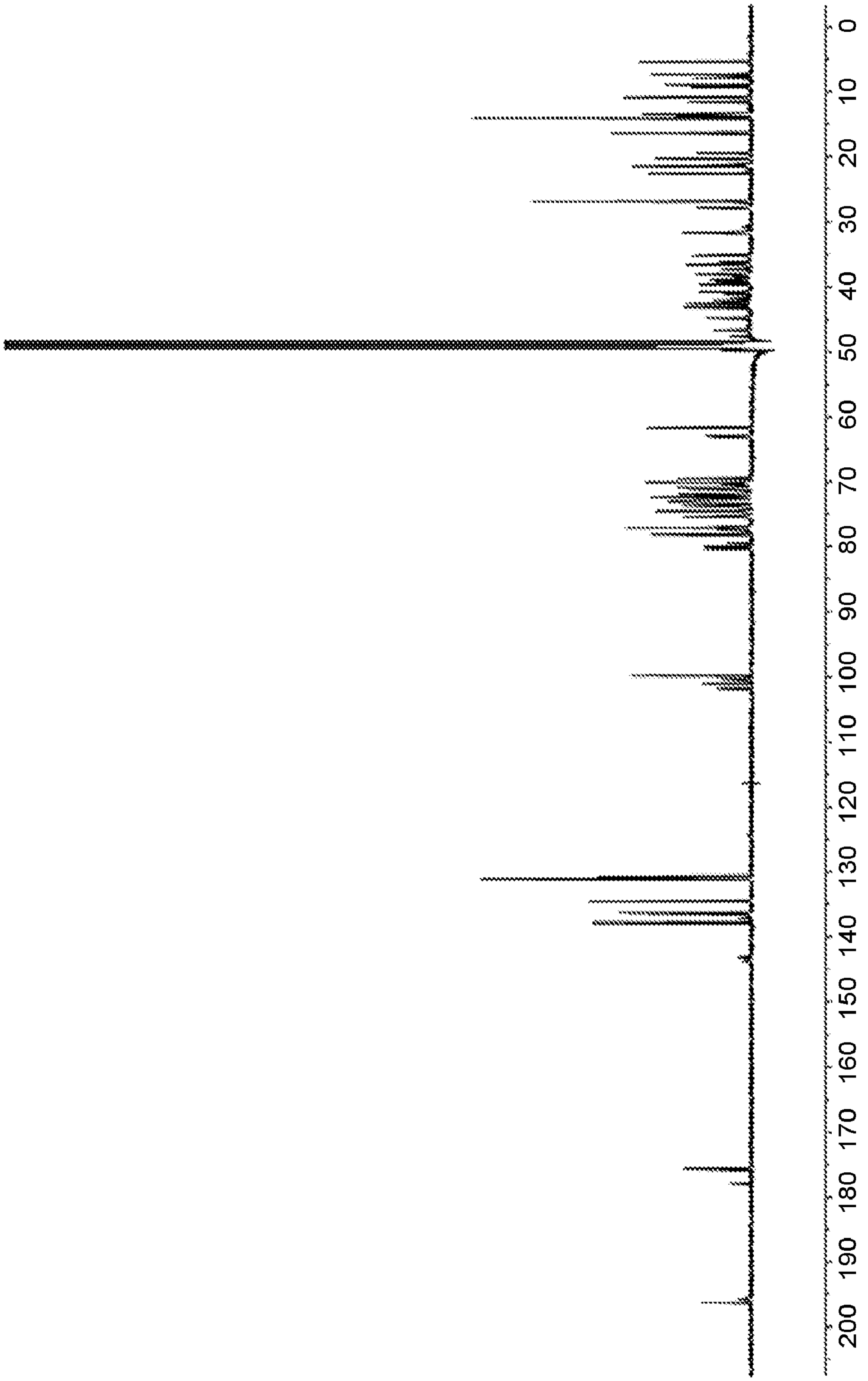
FIG. 8 shows a $^{13}$C-NMR spectrum of compound 1.
Figure 9:
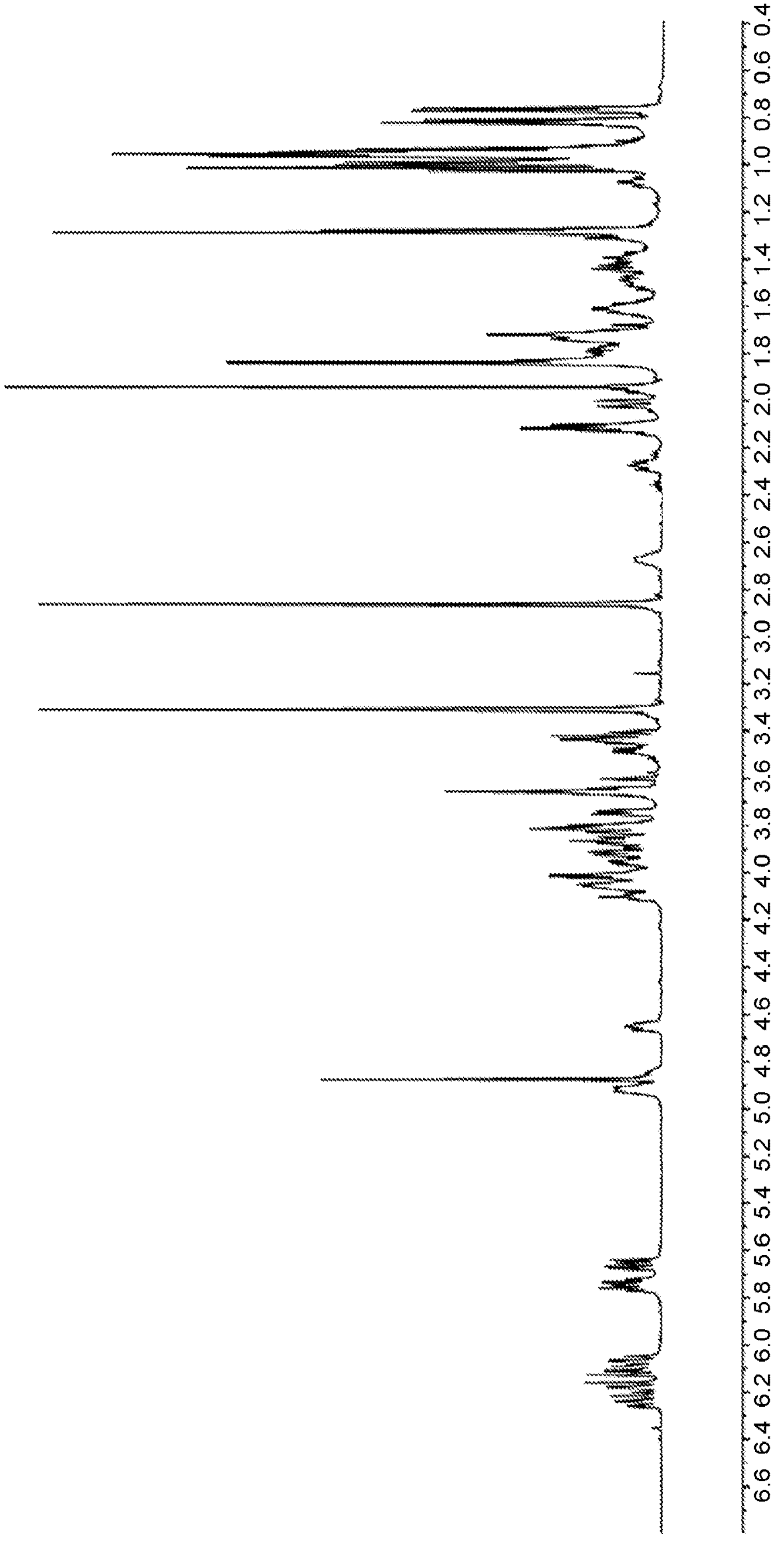
FIG. 9 shows a $^{1}$H-NMR spectrum of compound 2.
Figure 10:
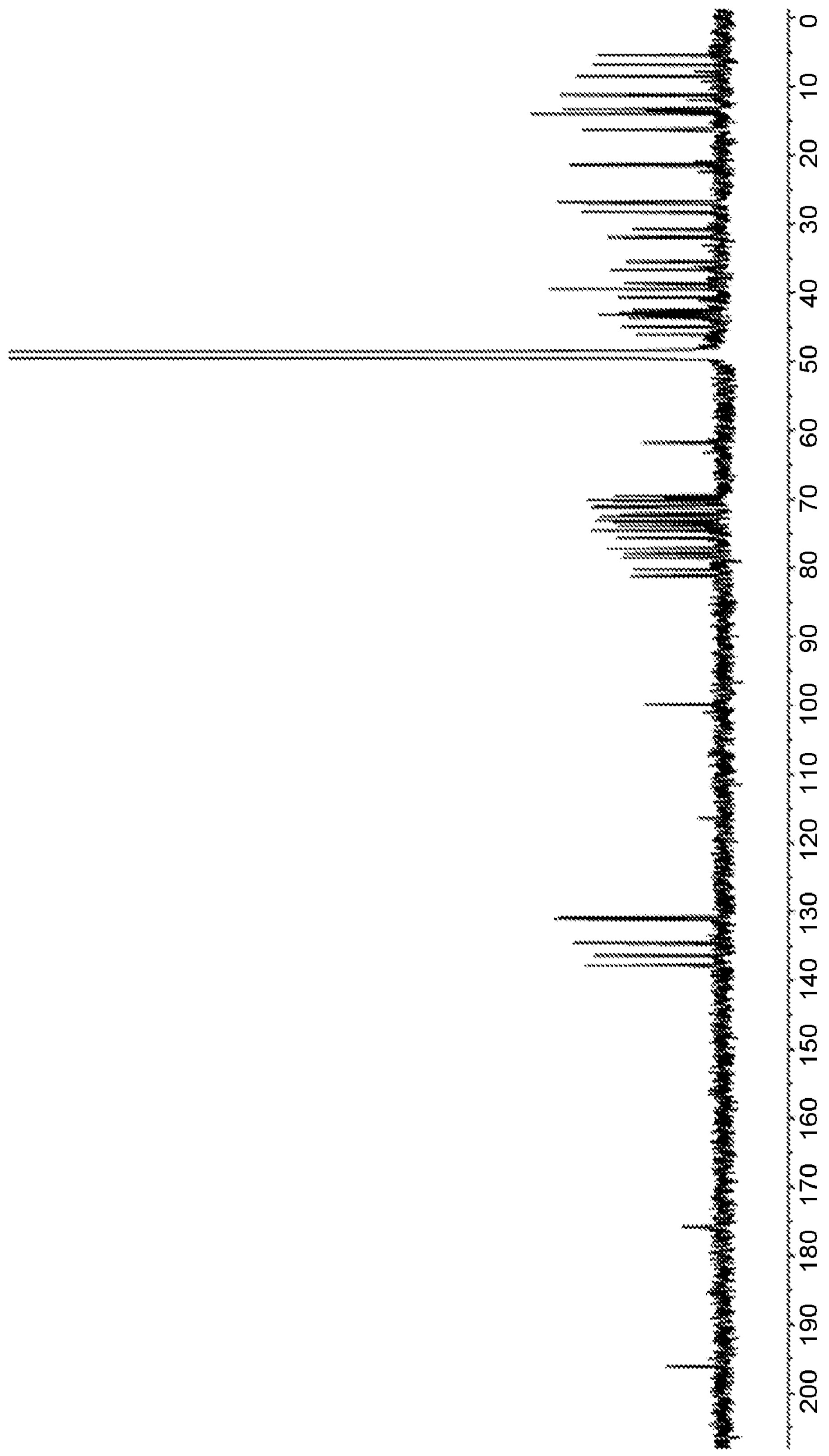
FIG. 10 shows a $^{13}$C-NMR spectrum of compound 2.
Figure 11:
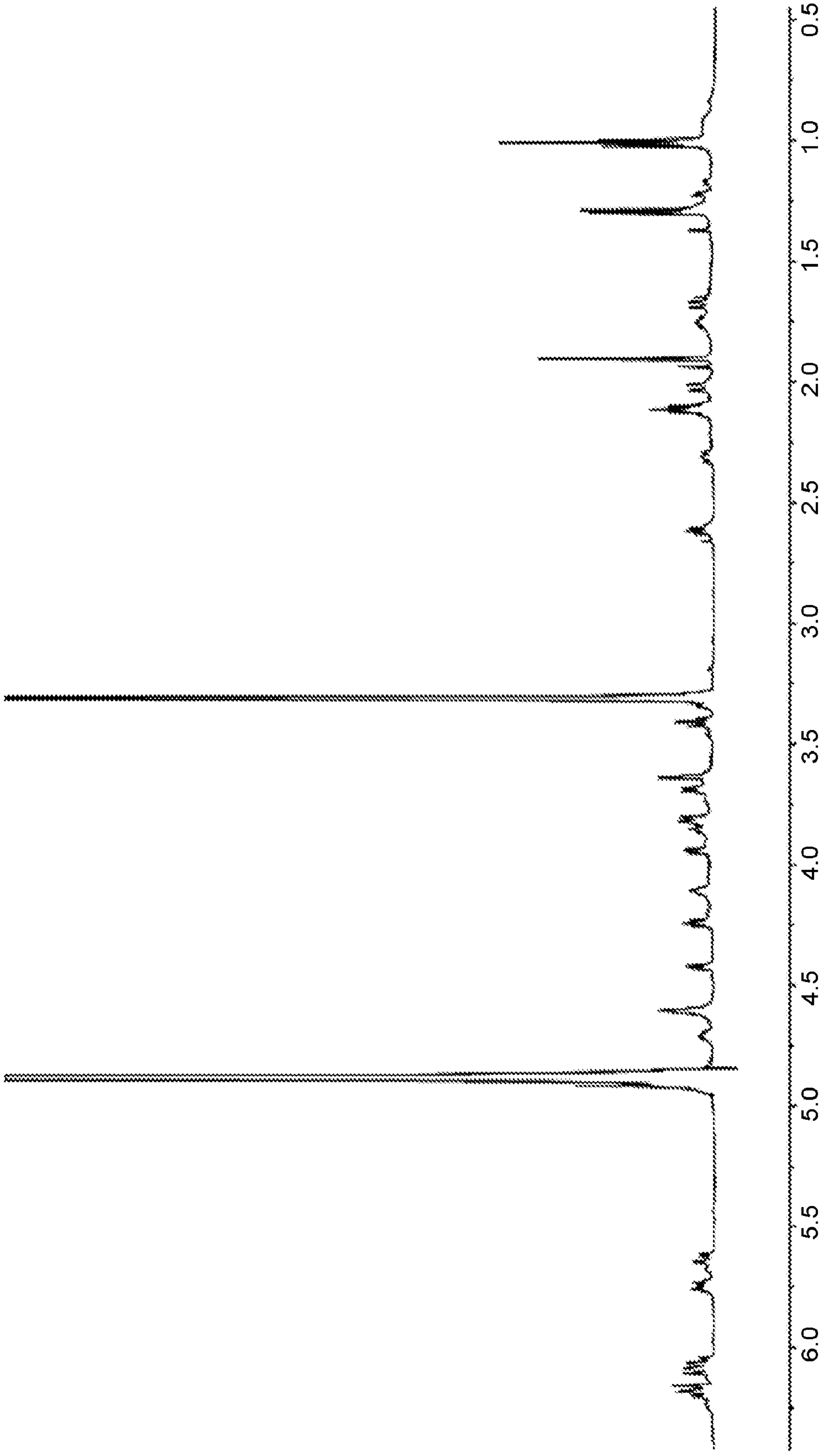
FIG. 11 shows a $^{1}$H-NMR spectrum of compound 3.
Figure 12:
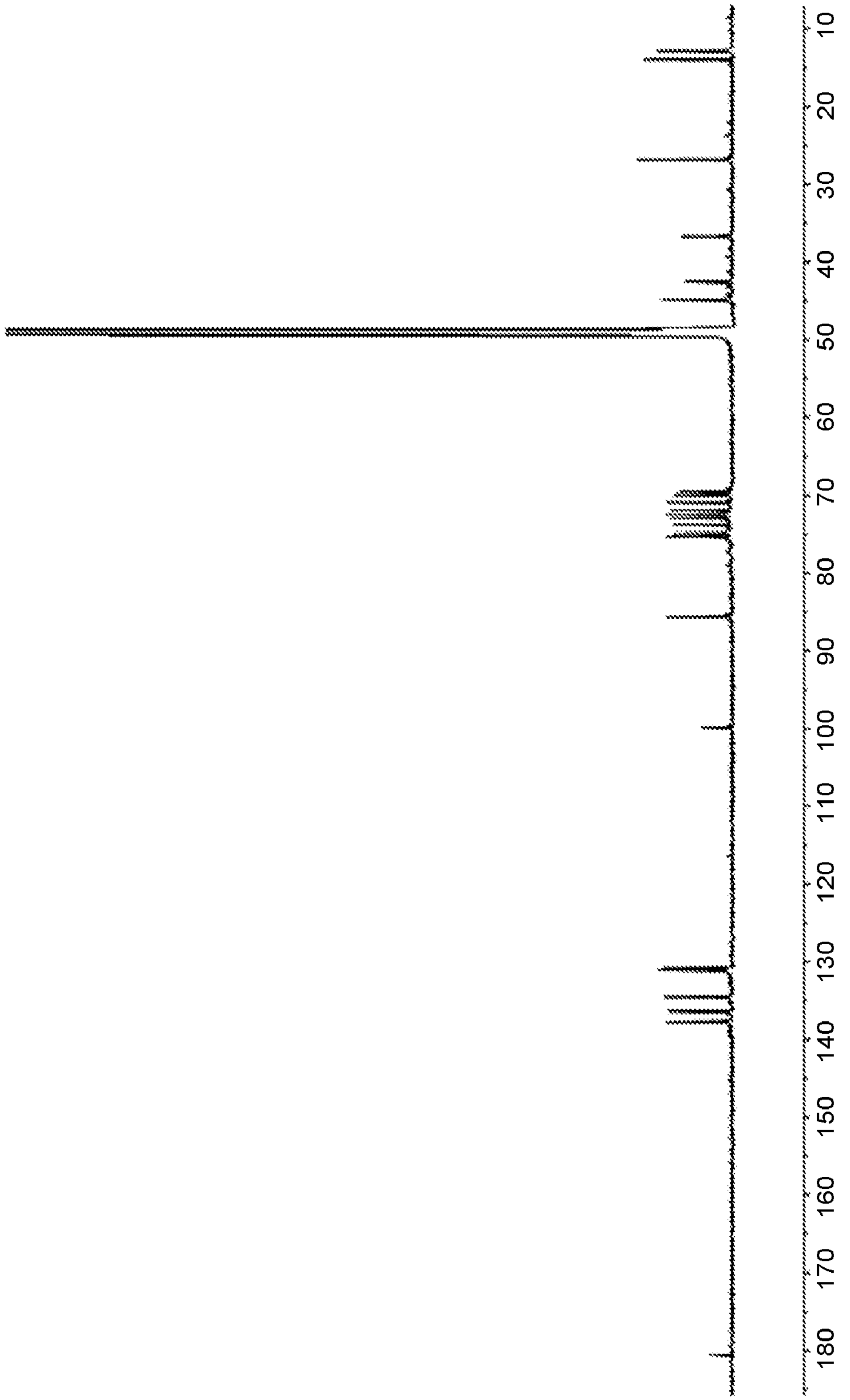
FIG. 12 shows a $^{13}$C-NMR spectrum of compound 3.

*Amycolatopsis* spp. strains GA6-003 and F10 were grown in parallel in R2YE medium and the cultures were sampled daily to measure the relative abundance of compound 1 and compound 2 by HPLC. In both strains, peak compound 2 levels were reached at day 4 and then subsided as compound 1 levels hit a sustained maximum level for the duration of the growth. Quantitation of compound 1 and compound 2 by HPLC at 254 nm for both GA6-003 and F10 strains is shown in FIG. 4. Average of n=3 with standard deviation plotted.

Example 5

This example shows NMR and MS data for compounds 1-4. Table 2 sets forth NMR data of compound 1 recorded at 500 MHz in $CD_3OD$, 278 K. Table 3 sets forth NMR data of compound 2 at 298 K 600 NMR in MeOD. Table 4 sets forth NMR data of compound 3 at 298 K 600 NMR in MeOD and Table 5 sets forth NMR data of compound 4 at 298 K 500 NMR in MeOD. Carbon numbering for compounds 1-3 is shown in FIG. 13. The spectral data and the formula of compound 4 are as set forth in FIG. 14-17.

TABLE 2

NMR data of compound 1 recorded at 500 MHz in $CD_3OD$, 278 K.

| No. | | $\delta_C$ | $\delta_H$ | $^{13}C$-$^{13}C$ COSY | $^1H$-$^1H$ COSY | HMBC | ROESY |
|---|---|---|---|---|---|---|---|
| 1 | $CH_3$ | 14.05 | 1.02 t (7.5) | C2 | H2 | C2, C3 | H2, |
| 2 | $CH_2$ | 26.90 | 2.12 m | C1, C3 | H1, H3, H4 | C1, C3, C4 | H1, H3, H4 |
| 3 | CH | 137.83 | 5.75 dt (14.6, 6.7) | C2, C4 | H2, H4 | C1, C2, C4, C5 | H2, H5 |
| 4 | CH | 130.72 | 6.07 dd (14.6, 10.3) | C3, C5 | H3, H5 | C2, C6 | H2, H6 |
| 5 | CH | 134.56 | 6.18 dd (14.6, 10.3) | C4, C6 | H4, H6 | C3, C7 | H3, H7 |
| 6 | CH | 131.09 | 6.11 dd (14.6, 10.4) | C5 | H5, H7 | C4, C8 | H4, H8 |
| 7 | CH | 131.09 | 6.24 dd (15.0, 10.4) | C8 | H6, H8 | C5, C9 | H5, H9 |
| 8 | CH | 136.32 | 5.66 dd (15.0, 6.5) | C7, C9 | H7, H9 | C6, C9, C10 | H6, H9, H10b, H10a |
| 9 | CH | 70.12 | 4.66 t-like (8.8) | C8, C10 | H7, H8, H10 | C7, C8, C10, C11 | H7, H8, H10b(w), H10a, H12 |
| 10 | $CH_2$ | 42.65 | a 2.01 dd (14.4, 2.0) | C9, C11 | H9 | C8, C9, C11, C12, C8 | H8, H9, H12 |
| | | | b 1.68 dd (14.4, 11.2) | | | | H8, H9, H12 |
| 11 | C | 99.84 | | C10, C12 | | | |
| 12 | CH | 74.50 | 3.66 s-like[A] | C11, C13 | H13 | C10, C11, C13, C14 | H9, H10a, H10b(w), H13 |
| 13 | CH | 72.35 | 3.82 dd (9.6, 2.5)[A] | C12 | H12, H14 | C12, C14, C15 | H12, H14, H15 |
| 14 | CH | 73.05 | 3.42 dd (9.8, 9.6)[A] | C15 | H13, H15 | C13, C15, C16 | H13, H15, H16a(w), H16b |
| 15 | CH | 70.87 | 3.87 dd (10.0, 9.8)[A] | C14, C16 | H14, H16 | C11, C13, C14, C16, C17 | H13, H14, H16a, H16b(w), H18 |
| 16 | $CH_2$ | 36.60 | a 2.29 m | C15, C17 | H15, H17 | C14, C15, C17, C18 | H14(w), H15, H17 |
| | | | b 1.77 m | | | | H14, H15(w), H17(w), H18 |
| 17 | CH | 69.53 | 4.10 m | C16, C18 | H16, H18 | C15, C16 | H16a, H16b(w), H18 |
| 18 | CH | 73.62 | 3.75 d (7.3)[A] | C17, C19 | H17, H19 | C16, C19, C20 | H15, H16b, H17, H19, H20 |

TABLE 2-continued

NMR data of compound 1 recorded at 500 MHz in $CD_3OD$, 278 K.

| No. | | $\delta_C$ | $\delta_H$ | $^{13}C$-$^{13}C$ COSY | $^1H$-$^1H$ COSY | HMBC | ROESY |
|---|---|---|---|---|---|---|---|
| 19 | CH | 71.11/71.08 | 4.02 d (7.3)$^A$ | C18, C20 | H18, H20 | C17, C18, C21 | H18, H20 |
| 20 | CH | 71.90 | 3.64 d (9.2)$^A$ | C19, C21 | H19, H21 | C18, C19, C21, C22 | H18, H19, H20, H21 |
| 21 | CH | 77.08 | 3.93 m | C20, C22 | H20, H22 | C19, C20, C22, C23, C50 | H20, H22, H23, H51 |
| 22 | CH | 35.25/35.22 | 2.10 m | C21, C23, C50 | H21, H23, H50 | C21, C23, C50 | H21, H23, H50 |
| 23 | CH | 80.01/79.96 | 3.63 m | C22, C24 | H22, H24 | C22, C24, C25, C50, C51 | H21, H22, H24, H25, H51 |
| 24 | CH | 43.19 | 1.84 m | C23, C25, C51 | H23, H25, H51 | C22, C23, C25, C26, C51 | H23, H25, H50, H51 |
| 25 | CH | 72.74/72.78 | 4.09 m | C24, C26 | H24, H26 | C23, C24, C26, C27, C51 | H23, H24 |
| 26 | $CH_2$ | 38.84/38.78 | 1.71 m, 1.49 m | C25, C27 | H25, H27 | C24, C25, C27, C28 | H27, H51 |
| 27 | CH | 71.00 | 4.04 m | C26, C28 | H26, H28 | C25, C28, C29 | H26 |
| 28 | $CH_2$ | 44.80/44.84 | 1.74 m, 1.59 m | C27, C29 | H27, H29 | C26, C27, C29, C30 | H29 |
| 29 | CH | 70.20/70.40 | 4.00 m/4.04 m | C28, C30 | H28, H30 | C28, C31, C33 | H28, H30 |
| 30 | $CH_2$ | 42.15/41.63 | 1.74 m, 1.58 m/1.88 m, 1.57 m | C29, C31 | H29, H31 | C28, C29, C31, C32 | H29, H52 |
| 31 | CH | 75.40/74.66 | 3.94 m/3.84 m | C30, C32 | H30 | C29, C30, C32, C33, C52 | H33, H52 |
| 32 | CH | 40.78/41.05 | 1.73 m/1.78 m | C31, C33, C52 | H33, H52 | C30, C31, C52 | H33, H53 |
| 33 | CH | 80.34/79.49 | 3.81 d (8.1)/4.05 d (9.9)$^A$ | C32, C34 | H32 | C31, C32, C34, C35, C52 | H31, H32, H35, H52, H53 |
| 34 | CH | 39.65/36.15 | 1.77 m/1.69 m | C33, C35, C53 | H35, H53 | C33, C35, C36, C53 | H52, H53, H54 |
| 35 | CH | 77.43/76.96 | 4.01 m/4.33 m | C34, C36 | H34, H36 | C33, C34, C37, C53, C54 | H33, H36, H37, H53 |
| 36 | CH | 38.02/37.35 | 1.97 m/2.09 m | C35, C37, C54 | H35, H37, H54 | C34, C37, C38, C54 | H35, H37, H53, H54 |
| 37 | CH | 75.35/72.96 | 3.67 m/3.61 m | C36, C38 | H36, H38 | C1', C36, C54 | H35, H36, H38, H54 |
| 38 | CH | 76.94/73.80 | 4.03 m/4.23 m | C37, C39 | H37, H39 | | H37, H39, H1', H54, H55 |
| 39 | $CH_2$ | 39.24/38.41 | 1.56 m, 1.44 m/1.74 m, 1.46 m | C38, C40 | H38 | C37, C38, C40, C41, C55 | H38, H55, H1' |
| 40 | CH | 27.80/27.96 | 1.82 m/1.79 m | C39, C41, C55 | H41, H55 | C38, C41, C56 | H1' |
| 41 | $CH_2$ | 46.71/47.62 | 1.41 m, 1.12 m/1.33 m, 1.18 m | C40, C42 | H40, H42 | C42, C55 | H42 |
| 42 | CH | 31.61/31.71 | 2.69 m/2.68 m | C41, C43, C56 | H41, H43, H56 | C56 | H41, H55, H56, H57 |
| 43 | CH | 143.15/143.72 | 5.68 m/5.71 m | C42, C44 | H42, H57 | C45, C57 | H57 |
| 44 | C | 137.09/136.53 | | C43, C45, C57 | | | |
| 45 | C | 196.22/195.75 | | C44, C46 | | | |
| 46 | C | 101.03/100.97 | | C45, C47, C58 | | | |
| 47 | C | 196.29 | | C46, C48 | | | |
| 48 | CH | 61.71 | 3.51 m | C47, C49 | H49 | C47, C49, C58, C59 | H49, H59 |
| 49 | $CH_3$ | 16.36/16.30 | 1.28 d (6.8) | C48 | H48 | C47, C48 | H48, H59 |
| 50 | $CH_3$ | 5.40/5.36 | 0.93 d (7.0)$^A$ | C22 | H22 | C21, C22, C23 | H20, H22, H24, |
| 51 | $CH_3$ | 10.91/10.88 | 0.81 d (6.9) | C24 | H24 | C23, C24, C25 | H23, H24, H25, H26, |
| 52 | $CH_3$ | 7.31/7.93 | 0.95 d (6.8)/0.92 d (6.8)$^A$ | C32 | H32 | C31, C32, C33 | H34, H30, H31, H33, H53 |
| 53 | $CH_3$ | 13.47/11.60 | 0.82 d (6.8)/0.77 d (6.8) | C34 | H34 | C33, C34, C35 | H32, H33, H34, H35, H36, H52 |
| 54 | $CH_3$ | 8.96/9.29 | 0.98 d (6.4)/0.99 d (6.4)$^A$ | C36 | H36 | C35, C36, C37 | H34, H36, H37, H38, H1' |
| 55 | $CH_3$ | 20.31/19.46 | 0.93 d (6.5)/0.92 d (7.0)$^A$ | C40 | H40 | C39, C40, C41 | H38, H39, H42, H1' |
| 56 | $CH_3$ | 21.50/21.30 | 1.01 d (6.6)/0.99 d (6.4)$^A$ | C42 | H41 | C41, C42, C43 | H42 |
| 57 | $CH_3$ | 13.86/13.61 | 1.83 s/1.80 s | C44 | | C43, C44, C45 | H42, H43 |
| 58 | C | 175.67 | | C46 | | | |
| 59 | $CH_3$ | 26.94 | 2.87 s | | | C48, C58 | H48, H49 |
| 1' | CH | 101.79/100.40 | 4.33 d (7.8)/4.34 d (7.4) | C2' | H2' | C38, C5', C3' | H38, H3', H5', H39, H40, H54, H55 |
| 2' | CH | 75.45/75.24 | 3.12 dd (9.4, 7.8)/3.10 dd (9.4, 7.4)$^A$ | C1', C3' | H1', H3' | C1', C3' | H4' |
| 3' | CH | 77.08/77.14 | 3.45 dd (9.6, 9.4)/3.39 dd (9.6, 9.4)$^A$ | C2', C4' | H2', H4' | C1', C2', C4', C5' | H1' |
| 4' | CH | 71.95/72.29 | 3.20 dd (9.8, 9.6)/3.14 dd (9.7, 9.6)$^A$ | C3', C5' | H3', H5' | C3', C5', C6' | H2' |
| 5' | CH | 78.10 | 3.29 m | C4', C6' | H4', H6' | C1', C3', C4', C6' | H1', H6' |
| 6' | $CH_2$ | 62.96/63.21 | 3.90 m, 3.61 m/3.91 m, 3.57 m | C5' | H5' | C5' | H5' |

$^A$Coupling constants from HSQC

W: means weak correlations

TABLE 3

NMR data of compound 2 at 298 K 600 NMR in MeOD

| No. | | $\delta_C$ | $\delta_H$ | COSY | HMBC | NOESY[B] |
|---|---|---|---|---|---|---|
| 1 | $CH_3$ | 14.00 | 1.01 t (7.5) | H2 | C2, C3 | H2 |
| 2 | $CH_2$ | 26.82 | 2.12 m | H1, H3, H4 | C1, C3, C4 | H1, H3, H4 |
| 3 | CH | 137.82 | 5.75 dt (14.7, 6.7) | H2, H4 | C1, C2, C5 | H2, H5 |
| 4 | CH | 130.73 | 6.04 ddt (14.7, 10.4, 1.4) | H3, H5 | C2, C6 | H2 |
| 5 | CH | 134.57 | 6.18 dd (14.7, 10.4) | H4, H6 | C3, C7 | H3 |
| 6 | CH | 131.08 | 6.11 dd (14.7, 10.4) | H5, H7 | C4, C8 | H8 |
| 7 | CH | 131.15 | 6.24 dd (15.2, 10.4, 1.2) | H6, H8 | C5, C9 | H9 |
| 8 | CH | 136.33 | 5.66 dd (15.2, 6.4) | H7, H9 | C6, C9, C10 | H6, H9, H10b, H10a |
| 9 | CH | 70.13 | 4.65 t (8.6) | H7, H8, H10 | C7, C8, C10, C11 | H7, H8, H10b(w), H10a, H12 |
| 10 | $CH_2$ | 42.86 | a 2.01 dd (14.6, 2.4) | H9 | C8, C11, C12 | H8, H9 |
| | | | b 1.70 dd (14.6, 10.6) | | | H8, H9(w), H12 |
| 11 | C | 99.89 | | | | |
| 12 | CH | 74.58 | 3.66 m | H13 | C11, C13, C14 | H10b, H9, H13 |
| 13 | CH | 72.50 | 3.82 dd (9.4, 3.3) | H12, H14 | C14 | H12, H15 |
| 14 | CH | 73.09 | 3.43 dd (9.7, 9.4) | H13, H15 | C13, C15, C16 | H16a(w), H16b |
| 15 | CH | 71.06 | 3.88 ddd (9.7, 10.0, 2.8) | H14, H16 | C14, C16, C17 | H13, H16a, H18 |
| 16 | $CH_2$ | 36.66 | a 2.28 dd (13.8, 8.1, 2.9) | H15, H17 | C15, C17, C18 | H14, H17 |
| | | | b 1.77 m | | | H14(w), H15, H17(w), H18 |
| 17 | CH | 69.90 | 4.10 dd (8.2, 5.9, 2.1) | H16, H18 | C15, C16 | H16a(w), H16b, H18, H20 |
| 18 | CH | 73.96 | 3.74 dd (6.6, 2.1) | H17, H19 | C19, C20 | H15, H16a, H17, H19, H20 |
| 19 | CH | 71.27 | 4.02 m | H18, H20 | C17, C18, C21 | H18, H20 |
| 20 | CH | 72.20 | 3.66 m | H19, H21 | C21, C22 | H17, H18, H19, H21, H50 |
| 21 | CH | 77.19 | 3.92 dd (8.9, 2.4) | H20, H22 | C19, C20, C23, C50 | H20, H23, H22, H50 |
| 22 | CH | 35.48 | 2.09 m | H21, H23, H50 | C21, C23, C50 | H21, H23, H50, H51 |
| 23 | CH | 80.21 | 3.65 m | H22, H24 | C50 | H22, H21, H25, H51 |
| 24 | CH | 43.19 | 1.83 m | H23, H25, H51 | C23, C25, C51 | H25, H51 |
| 25 | CH | 73.36 | 4.06 m | H24, H26 | C27, C51 | H23, H24, H26a, H51 |
| 26 | $CH_2$ | 39.45 | 1.73 m, 1.49 m | H25, H27 | C25, C27, C28 | H25, H27 |
| 27 | CH | 71.21 | 4.05 m | H26, H28 | | H26b, H28b |
| 28 | $CH_2$ | 44.94 | 1.73 m, 1.59 m | H27, H29 | C26, C27, C29, C30 | H27, H29 |
| 29 | CH | 70.40 | 4.01 m | H28, H30 | | H28a, H30b |
| 30 | $CH_2$ | 42.50 | 1.73 m, 1.62 m | H29, H31 | C28, C29, C31, C32 | H29, H31a |
| 31 | CH | 75.66 | 3.95 dt (8.4, 4.1) | H30, H32 | | H30, H52 |
| 32 | CH | 40.66 | 1.73 m | H31, H33, H52 | C52 | H33, H53 |
| 33 | CH | 81.15 | 3.80 overlapped | H32, H34 | C31, C35, C52 | H32, H35, H52, H53 |
| 34 | CH | 39.45 | 1.79 m | H33, H35, H53 | C33, C35 | H36, H53 |
| 35 | CH | 78.56 | 3.85 dd (5.8, 1.4, 1H) | H34, H36 | C33, C37, C54 | H33, H36, H37, H53 |
| 36 | CH | 38.65 | 1.95 m | H35, H37 | C37, C38, C54 | H34, H35, H37, H38, H53, H54 |
| 37 | CH | 77.90 | 3.44 dd (6.3, 3.5) | H36, H38 | C35, C54 | H35, H36, H38, H39, H54 |
| 38 | CH | 69.55 | 3.80 m | H37, H39 | | H36, H37, H39 |
| 39 | $CH_2$ | 43.62 | 1.40 dd (12.9, 8.3, 5.1) | H38, H40 | C37, C38, C40, C41, C55 | H37, H38 |
| 40 | CH | 28.27 | 1.83 m | H39, H41, H55 | | |
| 41 | $CH_2$ | 46.12 | a 1.44 m | H40, H42 | C42, C55 | |
| | | | b 1.07 dd (13.8, 10.2, 3.6) | | | |
| 42 | CH | 31.93 | 2.67 td (6.6, 3.3) | H41, H56 | | H55, H56, H57 |
| 43 | CH | 143.13[A] | NA | | | |
| 44 | C | 136.39[A] | | | | |
| 45 | C | 195.07[A] | | | | |
| 46 | C | 101.02 | | | | |
| 47 | C | 196.08 | | | | |
| 48 | CH | 61.84 | 3.48 q (6.8) | H49 | C47, C49, C58 | |
| 49 | $CH_3$ | 16.33 | 1.28 d (6.8) | H48 | C47, C48 | |
| 50 | $CH_3$ | 5.46 | 0.94 d (7.0) | H22 | C21, C22, C23 | H20, H21, H22 |
| 51 | $CH_3$ | 11.23 | 0.82 d (6.8) | H24 | C23, C24, C25 | H22, H23, H24, H25, H26b |
| 52 | $CH_3$ | 6.86 | 0.95 d (6.9) | H32 | C31, C32, C33 | H31, H33 |
| 53 | $CH_3$ | 13.34 | 0.77 d (6.8) | H34 | C33, C34, C35 | H32, H33, H34, H35, H36 |
| 54 | $CH_3$ | 8.52 | 0.96 d (6.8) | H36 | C35, C36, C37 | H36, H37 |
| 55 | $CH_3$ | 21.32 | 0.96 d (7.0) | H40 | C39, C40, C41 | H42 |
| 56 | $CH_3$ | 21.51 | 0.99 d (6.7) | H41 | C41, C42, C43 | H42 |
| 57 | $CH_3$ | 13.57 | 1.84 d (1.4) | | C43, C44, C45 | H42 |
| 58 | C | 175.78 | | | | |
| 59 | $CH_3$ | 26.99 | 2.86 s | | C48, C58 | |

[A]Data from HMBC

[B]Data recorded at 700 MHz

TABLE 4

| NMR data of compound 3 at 298 K 600 NMR in MeOD | | | | | | |
|---|---|---|---|---|---|---|
| No. | | $\delta_C$ | $\delta_H$ | COSY | Key HMBCs | NOESY |
| 1 | $CH_3$ | 14.0 | 1.01 t (7.4) | H2 | | |
| 2 | $CH_2$ | 26.8 | 2.11 m | H1, H3, H4 | | H4 |
| 3 | CH | 137.8 | 5.75 dt (15.3, 6.7) | H2, H4 | | H5 |
| 4 | CH | 130.7 | 6.08 dd (15.3, 10.3) | H3, H5 | | H2 |
| 5 | CH | 134.5 | 6.18 dd (15.0, 10.3) | H4, H6 | | H3 |
| 6 | CH | 131.1 | 6.10 dd (15.0, 10.3) | H5, H7 | | H8 |
| 7 | CH | 131.0 | 6.18 dd (15.2, 10.3) | H6, H8 | C9 | H9 |
| 8 | CH | 136.4 | 5.63 dd (15.2, 6.5) | H7, H9 | C9 | H6, H9, H10a, H10b |
| 9 | CH | 70.0 | 4.71 ddd (10.9, 6.5, 2.1) | H7, H8, H10 | C11 | H7, H8, H10a |
| 10 | $CH_2$ | 42.5 | a 2.02 dd (14.6, 2.1)<br>b 1.67 dd (14.6, 10.9) | H9 | C9, C11 | H8, H12 H8, H9 |
| 11 | C | 99.9 | | | | |
| 12 | CH | 74.9 | 3.64 d (3.3) | H13 | C11, C13, C14 | H10a, H13 |
| 13 | CH | 72.5 | 3.81 dd (9.5, 3.3) | H12, H14 | C14 | H12, H15(1DNOE) |
| 14 | CH | 73.0 | 3.41 dd (9.5, 9.5) | H13, H15 | C15, C13 | H16a, H16b |
| 15 | CH | 70.9 | 3.85 ddd (10.7, 9.5, 2.6) | H14, H16 | C11 | H13, H16b, H17 |
| 16 | $CH_2$ | 36.7 | a 2.31 ddd (13.7, 8.5, 2.6)<br>b 1.75 ddd (13.7, 10.8, 5.8) | H15, H17 | C14, C15, C17, C18 | H14, H17 H14, H15, H18 |
| 17 | CH | 69.5 | 4.11 ddd (8.5, 5.8, 2.0) | H16, H18 | | H16a, H18, H15 |
| 18 | CH | 73.7 | 3.69 dd (7.5, 2.0) | H17, H19 | C19, C20 | H16b, H17, H19 |
| 19 | CH | 71.9 | 3.94 dd (7.5, 2.2) | H18, H20 | C18, C20 | H18, H20 |
| 20 | CH | 85.7 | 4.42 dd (6.7, 2.2) | H19, H21 | C19, C21, C24 | H19, H22 |
| 21 | CH | 75.4 | 4.24 dd (8.0, 6.7) | H20, H22 | C19, C20, C24 | H23 |
| 22 | CH | 44.8 | 2.62 m | H21, H23 | C21 | H20, H23 |
| 23 | CH | 12.9 | 1.29 d (7.2) | H22 | C21 | H21, H22 |
| 24 | C | 180.6 | | | | |

TABLE 5

| NMR data of compound 4 at 298 K 500 NMR in MeOD | | | | | | | |
|---|---|---|---|---|---|---|---|
| No. | | $\delta_C$ | $\delta_H$ | $^3J_{H,H}{}^A$ | COSY | Key HMBCs | NOESY |
| 1 | $CH_3$ | 13.99 | 1.01 t (7.4) | t (7.4) | H2 | C2, C3 | H2 |
| 2 | $CH_2$ | 26.82 | 2.12 m | m | H1, H3, H4 | C1, C3, C4 | H1, H3, H4 |
| 3 | CH | 137.81 | 5.75 dt (14.9, 6.7) | dt (14.9, 6.9) | H2, H4 | C1, C2, C5 | H2, H5 |
| 4 | CH | 130.72 | 6.07 dd (14.9, 10.5) | dd (14.9, 10.5) | H3, H5 | C2, C6 | H2 |
| 5 | CH | 134.56 | 6.18 dd (14.6, 10.5) | dd (14.6, 10.5) | H4, H6 | C3, C7 | H3 |
| 6 | CH | 131.08 | 6.11 dd (14.6, 10.3) | dd (14.6, 10.4) | H5, H7 | C4, C5, C8 | H8 |
| 7 | CH | 131.14 | 6.24 ddd (15.1, 10.3, 1.2) | ddd (15.1, 10.4, 1.7) | H6, H8 | C5, C9 | H9 |
| 8 | CH | 136.33 | 5.66 dd (15.1, 6.4) | dd (15.1, 6.2) | H7, H9 | C6, C7, C9, C10 | H6, H9, H10a, |
| 9 | CH | 70.11 | 4.65 t-like (8.9) | m | H7, H8, H10 | C7, C8, C10, C11 | H7, H8, H10a, H12, H17 |
| 10 | $CH_2$ | 42.82 | a 2.01 dd (14.6, 2.4)<br>b 1.67 dd overlapped | dd (14.5, 11.0)<br>dd (14.5, 2.2) | H9 | C8, C9, C11, C12 | H8, H9, H12 |
| 11 | C | 99.88 | | | | | |
| 12 | CH | 74.58 | 3.65 d (3.3)$^A$ | d (3.5) | H13 | C10, C11, C13, C14 | H9, H10b, H13 |
| 13 | CH | 72.48 | 3.82 dd (9.5, 3.3) | dd (9.5, 3.5) | H12, H14 | C12, C14, C15 | H12 |
| 14 | CH | 73.10 | 3.42 t (9.5) | dd (9.5, 9.4) | H13, H15 | | H15, H16b |
| 15 | CH | 71.02 | 3.87 td (10.0, 2.8) | ddd (11.2, 9.4, 2.8) | H14, H16 | C11, C13, C14, C16, C17 | H14, H16a, H17, H18 |
| 16 | $CH_2$ | 36.65 | a 2.28 ddd (13.8, 8.2, 2.9)<br>b 1.75 m | ddd (14.2, 11.2, 6.0)<br>ddd (14.2, 8.4, 2.8) | H15, H17 | C14, C15, C17, C18 | H15, H18<br>H14, H17 |
| 17 | CH | 69.80 | 4.11 td (6.0, 3.1) | ddd (8.4, 6.0, 1.9) | H16, H18 | C16, C19 | H9, H15, H16b, H18, |
| 18 | CH | 73.86 | 3.74 dd (6.6, 2.0) | dd (6.8, 1.9) | H17, H19 | C16, C19, C20 | H15, H16a, H17, H19 |

TABLE 5-continued

NMR data of compound 4 at 298 K 500 NMR in MeOD

| No. | | $\delta_C$ | $\delta_H$ | $^3J_{H,H}{}^A$ | COSY | Key HMBCs | NOESY |
|---|---|---|---|---|---|---|---|
| 19 | CH | 71.21 | 4.02 m | dd (6.8, 1.6) | H18, H20 | C17, C18, C21 | H20 |
| 20 | CH | 72.15 | 3.64 dd (8.9, 1.5)$^A$ | dd (9.0, 1.6) | H19, H21 | C19, C24 | H19 |
| 21 | CH | 77.15 | 3.92 dd (8.9, 2.5) | dd (9.0, 2.6) | H20, H22 | C19, C20, C22, C23, C36 | H22, H36 |
| 22 | CH | 35.45 | 2.09 m | m | H21, H23, H36 | C21, C23, C36 | H21, H23, H24, H36, H37 |
| 23 | CH | 80.05 | 3.65 m | m | H22, H24 | C21, C24, C36 | H22, H25, H36, H37 |
| 24 | CH | 43.21 | 1.82 m | m | H23, H25, H37 | C23, C25, C37 | H22, H25, H36, H37, H26b |
| 25 | CH | 73.21 | 4.06 m | ddd (9.9, 4.9, 2.0) | H24, H26 | C37, C27 | H23, H24, H26a, H37, H26b(W) |
| 26 | $CH_2$ | 39.26 | a 1.72 m | ddd (14.2, 9.9, 7.8) | H25, H27 | C24, C25, C27, C28 | H25 |
| | | | b 1.48 ddd (14.2, 10.3, 7.6) | ddd (14.2, 4.9, 2.6) | | | H24 |
| 27 | CH | 71.21 | 4.03 m | m | H26, H28 | C25, C29 | H28 |
| 28 | $CH_2$ | 45.04 | 1.72 m | ddd (14.2, 8.0, 8.0) | H27, H29 | C26, C27, C29, C30 | |
| | | | 1.60 m | ddd (14.2, 4.6, 4.6) | | | |
| 29 | CH | 70.33 | 3.98 m | m | H28, H30 | C27, C28, C30, C31 | |
| 30 | $CH_2$ | 42.87 | 1.66 m | m | H29, H31 | C28. C29, C31, C32 | |
| 31 | CH | 74.02 | 3.97 m | overlapped | H30, H32 | C29, C32, C33, C38 | H33, H34, H38 |
| 32 | CH | 42.26 | 1.61 m | m | H31, H33, H38 | C31, C33, C38 | H38, H39 |
| 33 | CH | 77.76 | 3.66 m | overlapped | H32, H34 | C35, C34, C31, C32, C38, C39 | H31, H34, H38, H39 |
| 34 | CH | 45.48 | 2.48 qd (6.9, 1.3) | | H33, H39, H39 | C32, C33, C35, C39 | H31, H33, H38, H39 |
| 35 | | 184.06 | | | | | |
| 36 | $CH_3$ | 5.47 | 0.94 d (7.0) | d (7.2) | H22 | C21, C22, C23 | H21, H22, H23, H24 |
| 37 | $CH_3$ | 11.12 | 0.82 d (6.9) | d (7.1) | H24 | C23, C24, C25 | H22, H23, H24, H25 |
| 38 | $CH_3$ | 7.80 | 0.96 d (6.9) | d (7.0) | H32 | C31, C32, C33 | H31, H32, H33, H34 |
| 39 | $CH_3$ | 16.14 | 1.16 d (7.1) | d (7.3) | H34 | C33, C34, C35 | H32, H34 |

[A]coupling constants observed by 2D j-coupling
w: weak correlation

Example 6

This example demonstrates the Minimum Inhibitory Concentration (MIC) of compounds 1-3 against exemplary gram positive bacteria, gram negative bacteria, and fungi.

The compounds were assayed against Gram-positive bacteria *Staphylococcus aureus* (Sa), methicillin-resistant Sa (MRSA), *Enterococcus faecalis*, and Vancomycin-resistant *E. faecalis*; the Gram-negative bacteria *Escherichia coli* and *Pseudomonas aeruginosa*; and the fungi *Candida albicans* and Amphotericin B-resistant *C. albicans*.

The growth conditions were adapted from the CLSI protocols for broth dilution susceptibility assays. A culture of *S. aureus* ATCC 29213 was diluted with MHII broth to an inoculum of ~$5\times10^5$ CFU/mL. Cultures were grown in 100 μL in round-bottom 96-well plates with increasing concentrations of test or control compound. Plates were gently rocked at 37° C. overnight and then 50 μL of each culture was spread onto TSA plates without antibiotic. The plates were incubated at 37° C. overnight and then examined for bacterial growth. Similarly, an inoculum of *C. albicans* ATCC 28517 or *C. auris* ATCC MYA-5001 was prepared in RPMI-1640 with 165 mM MOPS at $0.5\times10^3$-$2.5\times10^3$ CFU/mL. Cultures were grown in 200 μL in round-bottom 96-well plates with increasing concentrations of test or control compound. Plates were gently rocked at 35° C. overnight and then 50 μL of each culture was spread onto Sabouraud dextrose agar (SDA) plates without compound. The plates were incubated at 35° C. overnight and then examined for fungal growth.

The results are set forth in Table 6.

TABLE 6

Minimum Inhibitory Concentration (MIC) of Compounds 1-3

| | | MIC,[c] micrograms/mL | | |
|---|---|---|---|---|
| | | 2 | 1 | 3 |
| Species | ATCC #[b] | 1193 | 1355 | 1036 |
| Gram-positive bacteria[c] | | | | |
| *Staphylococcus aureus* (Sa) | 29213 | 2 | >128 | 32 |
| MRSA, methicillin-resistant Sa | 43300 | 2 | >128 | 64 |
| *Enterococcus faecalis* | 29212 | 8 | >128 | nd[d] |
| Vancomycin-resistant *E. faecalis* | 51299 | 8 | >128 | nd |

TABLE 6-continued

Minimum Inhibitory Concentration (MIC) of Compounds 1-3

| Species | ATCC #[b] | MIC,[c] micrograms/mL 2 1193 | 1 1355 | 3 1036 |
|---|---|---|---|---|
| Gram-negative bacteria | | | | |
| *Escherichia coli* | 25922 | >128 | >128 | nd |
| *Pseudomonas aeruginosa* | 27853 | >128 | >128 | nd |
| Fungi[d] | | | | |
| *Candida albicans* | 28517 | 8 | >128 | 128 |
| Amphotericin B-resistant *C. albicans* | 200955 | 8 | >128 | nd |
| *Candida auris* | MYA-5001 | 16 | >128 | >128 |

[a]Note that if compounds were not active against the wild type drug-resistant strain, no further assays were carried out on drug-resistant strains.
ATCC, American Type Culture Collection, Manassas VA
[b]MICs were determined using the CLSI (Clinical Laboratory & Standards Institute) recommended protocols for broth dilution susceptibility assays
[c]Antibiotic controls:
*S. aureus*: oxacillin = 0.25-0.5 ug/mL
MRSA: vancomycin = 0.5-1 ug/mL
*E. faecalis*: vancomycin = 2 ug/mL
VRE: ciprofloxacin = 0.25-0.5 ug/mL
*C. albicans*: amphotericin B = 2 ug/mL
Amphotericin B-resistant *C. albicans*: fluconazole = 0.125 ug/mL
*C. auris*: fluconazole = 1 ug/mL
[d]nd = not determined.

Example 7

This example demonstrates a mechanism of action of compound 2 of the invention.

Figure 18:
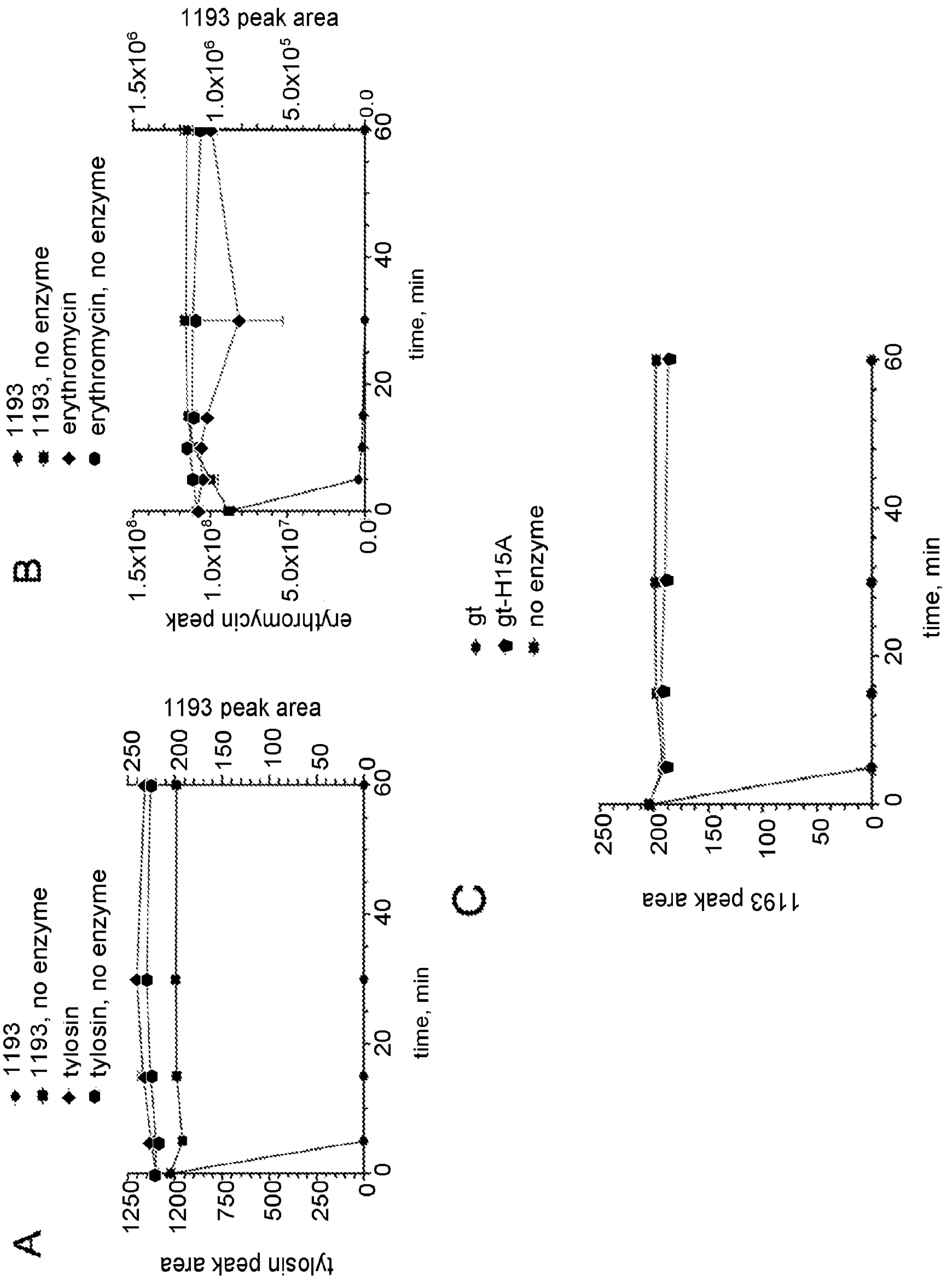

The results set forth in FIG. 18 show that compound 2 is bactericidal against *S. aureus* and fungicidal against *C. albicans* and *C. auris*. After treatment with concentrations of compound 2 at or nearing the MIC, no viable organism could be recovered.

FIG. 19-20 show bactericidal and fungicidal activities of compound 2. FIG. 19A-C show the bactericidal activity of compound 2 against *S. aureus* ATCC 29213. FIG. 19A displays the activity of oxacillin, bactericidal control, MIC in the experiment=2 μg/mL. FIG. 19B displays the activity of chloramphenicol, bacteriostatic control, MIC in the experiment=8 μg/mL. FIG. 19C displays the activity of compound 2, MIC in the experiment=2 μg/mL. FIG. 20A-B show the fungicidal activity of compound 2. FIG. 20A displays the activity against *C. albicans* ATCC 28517, MIC in the experiment=8 μg/mL. FIG. 20B displays the activity against *C. auris* ATCC MYA-5001, MIC in the experiment=16 μg/mL.

Example 8

This example illustrates that a 139 kb hybrid polyketide synthase/nonribosomal peptide synthetase (PKS/NRPS) biosynthetic gene cluster (BGC) encodes the enzymes necessary to produce compounds 1 and 2. The glycosyltransferase gene was cloned from the BGC associated with the polyketides of the invention. A method was developed to recombinantly express and purify the enzyme. See Reference (1)-(4) cited below.

Glycosyltransferase expression vector cloning: An expression vector pET28b-gt was constructed by cloning the glycosyltransferase gene into pET28b (Novagen) with a C-terminal 6-His tag using the NEBuilder HiFi DNA Assembly kit (New England Biolabs). The glycosyltransferase gene was PCR amplified from F10 genomic DNA with primers that appended 5' and 3' overhangs homologous to the pET28b multiple cloning site. The linearized pET28b vector was prepared by restriction enzyme digestion with NcoI and XhoI. After cloning and confirmation by Sanger sequencing, pET28b-gt was transformed into *E. coli* BL21 (DE3) for protein expression. The expression vector pET28b-gt-H15A was created from pET28b-gt with site-directed mutagenesis using overlapping primers and the QuikChange II kit.

Glycosyltransferase recombinant protein purification: An overnight culture of the glycosyltransferase expression strain in Luria-Bertani broth (LB) was used to inoculate 2 L LB with a 1:100 dilution (v/v). The culture was grown at 37° C. to OD600=0.5-0.7 and 0.1 mM isopropyl β-d-1-thiogalactopyranoside (IPTG) was added to induce protein expression for 4 hours. Cells were harvested by centrifugation, suspended in 20 mL phosphate-buffered saline (PBS) and stored at −80° C. For purification, the cells were thawed, lysed (lysozyme, DNase, MgCl2, phenylmethylsulfonyl fluoride (PMSF), and sonication), and cellular debris was removed by centrifugation. The glycosyltransferase was purified from the clarified lysate in two chromatographic steps on an AKTA Pure 25 FPLC. First, the lysate was loaded onto a 5 mL His-trap affinity column, washed with the above buffer containing 10 mM imidazole, and eluted with a gradient from 10 to 500 mM imidazole over 100 mL. The eluted fractions containing the glycosyltransferase were confirmed by SDS-PAGE, pooled, and concentrated and buffer exchanged to remove imidazole in a 10000 Da MW centrifugal filter device. The sample was run on a HiLoad Superdex 75 pg 16/600 size exclusion column with 50 mM HEPES pH 6.8/50 mM NaCl/10% glycerol. Protein purity was confirmed by SDS-PAGE. The purified glycosyltransferase was concentrated and flash frozen in aliquots at 80° C. The same protocol was used to purify the catalytically inactive H15A mutant.

Glycosyltransferase assay: Compound 2 was converted into compound 1 with the following reaction conditions: PBS, 500 μM UDP-glucose, and 100 μM of compound 2 at 30° C. for 2 to 30 min. Aliquots of the reaction mixture was taken at desired time points to measure the levels of compounds 2 and 1 by analytical HPLC with UV (254 nm) or MS detection. Samples were taken from the reaction tube, quenched with an equal volume of methanol, centrifuged for 5 min at 20,000 g, and 20 μL is injected onto the analytical HPLC-MS system previously described in the EIR. To investigate substrate specificity, UDP-glucose was changed out for UDP-galactose and compound 2 was changed out for erythromycin or tylosin. The putative products of these reactions were identified by MS detection of the theoretical m/z.

The PKS/NRPS enzyme robustly converted compound 2 into compound 1. An assay was developed where the assay conditions were suitable to completely and quickly glycosylate compound 2. Sequence homology to other family members showed that His-15 is required for catalysis. Mutation of this residue to Ala abolished activity. The glycosyltransferase prefers UDP-glucose over UDP-galactose for the sugar donor. It has no activity on the macrolide antibiotics erythromycin and tylosin, thereby suggesting specificity for the chemical scaffold of the polyketides. These results validate that the BGC is responsible for producing the polyketides.

The results are shown in FIG. 18. The glycosyltransferase encoded in the polyketide's BGC converted compound 2 into compound 1 with specificity over other antibiotics. FIG. 18A and FIG. 18B show complete conversion of compound 2 to compound 1 upon treatment with the *Amycolatopsis* glycosyltransferase, and no activity on tylosin or erythromycin, other macrolide antibiotics. The levels of compound 1 were quantified by HPLC with UV detection at 254 nm. FIG. 18C confirms the catalytic role of His-15 in glycosyl transferase activity. n=3 with standard deviation plotted.

SEQUENCE LISTING

SEQ ID NO: 1

GCAGTCGAACGCTGAACCGGTTTCGGCCGGGGATG

AGTGGCGAACGGGTGAGTAACACGTGGGTAATCTG

CCCTGTACTCTGGGATAAGCCTGGGAAACTGGGTC

TAATACCGGATACGACCACTGCAGGCATCTGTGGT

GGTGGAAAGTTCCGGCGGTATGGGATGAACCCGCG

GCCTATCAGCTTGTTGGTGGGGTAATGGCCTACCA

AGGCGACGACGGGTAGCCGGCCTGAGAGGGTGACC

GGCCACACTGGGACTGAGACACGGCCCAGACTCCT

ACGGGAGGCAGCAGTGGGGAATATTGCACAATGGG

CGCAAGCCTGATGCAGCGACGCCGCGTGAGGGATG

ACGGCCTTCGGGTTGTAAACCTCTTTCGCCAGGGA

CGAAGCGAGAGTGACGGTACCTGGATAAGAAGCAC

CGGCTAACTACGTGCCAGCAGCCGCGGTAATACGT

AGGGTGCGAGCGTTGTCCGGAATTATTGGGCGTAA

AGAGCTCGTAGGCGGTTTGTCGCGTCGGCCGTGAA

ATCTCCACGCTTAACGTGGAGCGTGCGGTCGATAC

GGGCAGACTTGAGTTCGGCAGGGGAGACTGGAATT

CCTGGTGTAGCGGTGAAATGCGCAGATATCAGGAG

-continued

GAACACCGGTGGCGAAGGCGGGTCTCTGGGCCGAT

ACTGACGCTGAGGAGCGAAAGCGTGGGGAGCGAAC

AGGATTAGATACCCTGGTAGTCCACGCTGTAAACG

TTGGGCGCTAGGTGTGGGCGACATTCCACGTTGTC

CGTGCCGTAGCTAACGCATTAAGCGCCCCGCCTGG

GGAGTACGGCCGCAAGGCTAAAACTCAAAGGAATT

GACGGGGGCCCGCACAAGCGGCGGAGCATGTGGAT

TAATTCGATGCAACGCGAAGAACCTTACCTGGGCT

TGACATGCGCCAGACATCCCCAGAGATGGGGCTTC

CCTTGTGGTTGGTGTACAGGTGGTGCATGGCTGTC

GTCAGCTCGTGTCGTGAGATGTTGGGTTAAGTCCC

GCAACGAGCGCAACCCTTATCCTACGTTGCCAGCG

CGTCATGGCGGGGACTCGTGGGAGACTGCCGGGGT

CAACTCGGAGGAAGGTGGGGATGACGTCAAGTCAT

CATGCCCCTTATGTCCAGGGCTTCACACATGCTAC

AATGGCTGGTACAGAGGGCTGCGATACCGCGAGGT

GGAGCGAATCCCTTAAAGCCGGTCTCAGTTCGGAT

CGCAGTCTGCAACTCGACTGCGTGAAGTCGGAGTC

GCTAGTAATCGCAGATCAGCAACGCTGCGGTGAAT

ACGTTCCCGGGCCTTGTACACACCGCCCGTCACGT

CATGAAAGTCGGTAACACCCGAAGCCCATGGCCCA

ACCCGCAAGGGAGGGAGTGGTCGAAGG.

SEQ ID NO: 2

GACTTCGTCCAATCGCCAGTCCCACCTTCGACCAC

TCCCTCCCTTGCGGGTTGGGCCATGGGCTTCGGGT

GTTACCGACTTTCATGACGTGACGGGCGGTGTGTA

CAAGGCCCGGGAACGTATTCACCGCAGCGTTGCTG

ATCTGCGATTACTAGCGACTCCGACTTCACGCAGT

CGAGTTGCAGACTGCGATCCGAACTGAGACCGGCT

TTAAGGGATTCGCTCCACCTCGCGGTATCGCAGCC

CTCTGTACCAGCCATTGTAGCATGTGTGAAGCCCT

GGACATAAGGGGCATGATGACTTGACGTCATCCCC

ACCTTCCTCCGAGTTGACCCCGGCAGTCTCCCACG

AGTCCCCGCCATGACGCGCTGGCAACGTAGGATAA

GGGTTGCGCTCGTTGCGGGACTTAACCCAACATCT

CACGACACGAGCTGACGACAGCCATGCACCACCTG

TACACCAACCACAAGGGAAGCCCCATCTCTGGGGA

TGTCTGGCGCATGTCAAGCCCAGGTAAGGTTCTTC

GCGTTGCATCGAATTAATCCACATGCTCCGCCGCT

TGTGCGGGCCCCCGTCAATTCCTTTGAGTTTTAGC

CTTGCGGCCGTACTCCCCAGGCGGGGCGCTTAATG

-continued

CGTTAGCTACGGCACGGACAACGTGGAATGTCGCC

CACACCTAGCGCCCAACGTTTACAGCGTGGACTAC

CAGGGTATCTAATCCTGTTCGCTCCCCACGCTTTC

GCTCCTCAGCGTCAGTATCGGCCCAGAGACCCGCC

TTCGCCACCGGTGTTCCTCCTGATATCTGCGCATT

TCACCGCTACACCAGGAATTCCAGTCTCCCCTGCC

GAACTCAAGTCTGCCCGTATCGACCGCACGCTCCA

CGTTAAGCGTGGAGATTTCACGGCCGACGCGACAA

ACCGCCTACGAGCTCTTTACGCCCAATAATTCCGG

ACAACGCTCGCACCCTACGTATTACCGCGGCTGCT

GGCACGTAGTTAGCCGGTGCTTCTTATCCAGGTAC

CGTCACTCTCGCTTCGTCCCTGGCGAAAGAGGTTT

ACAACCCGAAGGCCGTCATCCCTCACGCGGCGTCG

CTGCATCAGGCTTGCGCCCATTGTGCAATATTCCC

CACTGCTGCCTCCCGTAGGAGTCTGGGCCGTGTCT

CAGTCCCAGTGTGGCCGGTCACCCTCTCAGGCCGG

CTACCCGTCGTCGCCTTGGTAGGCCATTACCCCAC

CAACAAGCTGATAGGCCGCGGGTTCATCCCATACC

GCCGGAACTTTCCACCCCCGAAGATGCCCCCAAAG

GTCGTATCCGGTATTAGACCCAGTTTCCCAGGCTT

ATCCCAGAGTACAGGGCAGATTACCCACGTGTTAC

TCACCCGTTCGCCACTCATCCCCGGCCGAAACCGG

TTCAGCGTTCGACTGCA.

F10 glycosyltransferase gene sequence

SEQ ID NO: 3

ATGGGCAAGCACATCGCTTTCGTCAGCATCCCGGC

GCAGGGCCACGTGAATCCCGCGCTGCCGCTGGTGT

CCGAGCTGGTCGCGCGCGGGCACCGGGTCAGCTAC

GCGACCGCGCCGGCCCGGCTCGACCAGGTCGCCGC

GGCGGGCGCGGAGCCGGTGCCGGCTCCGTTCCGGC

TGCCGCTGCCGCCCGGGGACGGCAAACTGCTCGAC

GCCCGCACCGTCGGCCTGCGGTTCGAGGAGTTCTA

CGCATCGGTCGTCGAGGTCTTCCCCCGGCTGGTGG

AGCATTTCGCCGCGGACCGGCCCGACCTGTTCTGC

GTCGACGCGATGACGCCGGTCGGCCGGATGGTCGC

GCAGAAACTCGGCGTCCCGCTGGCCGCCATGCATC

CCACCCACGCCAGCAACAAGGAATTCTCGCTCCGT

GCCACCGTGATGGGCATCGAGGGAGCGCTTTCGGA

CCCGGCTTCGGTCGAGGTGGTCGTCCGCGCCGTGC

AGGAGGTGGGCCGCAAGGTCCGCGCTTTCGCCGAG

GAAAACGGGGTCGACCCCGATTACGACATGTTCGA

-continued

CTATCCGGCCGACCACAACCTCGTTTTCATCCCCA

GGGAATTCCAGATCAAGGGGGAGACTTTCGACGAC

CGGTTCCGTTTCCCGGGGCCGACGATCGTCGAACG

GCCCGATGCCGGGCATTGGCAGCCCGCCGGGAAAC

CGCTGCTGTACATCTCGCTCGGGACTTTGTTCAAC

GACAACCTGAAGTTCTACCGCAGCTGCCTGGACGC

TTTCGGCGGCACGGAATGGCAGGTGGCGATGTCGG

TGGGCGCGGAGGTCGACCTCGCGGCGCTGGGCCCG

GTGCCGGGCAACATCGACGTGCGGCCGCATTTCCC

GCAGCTCGAAGTGCTGCGCGAGGCCTCGGCATTCG

TCTCGCACTGCGGCATGAACTCGACGATGGAGGCG

CTGTTCTTCGGGGTGCCGCTGGTCGGGGTGCCGCA

GCAGGCCGAGCAGCTGATCAACGCCGAACGCGCCG

CGGAGCTGGGCTTCGGCACGGTCCTCGCGCCGGAG

GAGCTGACCGCGGCGCGGCTGCGGGAGAGCGTGGA

AGCGGTCGCCGCCGACGAGCGGATCCGCGCGAACC

TCGACGAAATCAGTGCCAAGCTGCGGAAACGCCGG

GGCGCGGTGCTGGCGGCGGACGCGCTGCTGGCGCA

ACTGGACCGAGCGGCGGCGGACGCGCTGCCGGACT

GA.

GA6-003 glycosyltransferase gene sequence

SEQ ID NO: 4

ATGGGCAAGCACATCGCTTTCGTCAGCATCCCGGC

GCAGGGCCACGTGAATCCCGCGCTGCCGCTGGTGT

CCGAGCTGGTCGCGCGCGGGCACCGGGTCAGCTAC

GCGACCGCGCCGGCCCGGCTCGACCAGGTCGCCGC

GGCGGGCGCGGAGCCGGTGCCGGCTCCGTTCCGGC

TGCCGCTGCCGCCCGGGGACGGCAAACTGCTCGAC

GCCCGCACCGTCGGCCTGCGGTTCGAGGAGTTCTA

CGAATCGGTCGTCGAGGTCTTCCCCCGGCTGGTGG

AGTATTTCGCCGCGGACCGGCCCGACCTGTTCTGC

GTCGACGCGATGACGCCGGTCGGCCGGATGGTCGC

GCAGAAACTCGGCGTCCCGCTGGCCGCCATGCATC

CCACCCACGCCAGCAACAAGGAATTCTCGCTCCGT

GCCACCGTGATGGGCATCGAGGGAGCGCTTTCGGA

CCCGGCTTCGGTCGAGGTGGTCGTCCGCGCCGTGC

AGGAGGTGGGCCGCAAGGTCCGCGCTTTCGCCGAG

GAAAACGGGGTCGACCCCGATTACGACATGTTCGA

CTATCCGGCCGACCACAACCTCGTTTTCATCCCCC

GGGAATTCCAGATCAAGGGGGAGACTTTCGACGAC

CGGTTCCGTTTCCCGGGGCCGACGATCGTCGAACG

GCCCGATGCCGGGCATTGGCAGCCCGCCGGGAAAC

-continued

CGCTGCTGTACATCTCGCTCGGGACTTTGTTCAAC

GACAATCTGAAGTTCTACCGCAGCTGCCTGGACGC

TTTCGGCGGCACGGAATGGCAGGTGGCGATGTCGG

TGGGCGCGGAGGTCGACCTCGCGGCGCTGGGCCCG

GTGCCGGGCAACATCGACGTGCGGCCGCATTTCCC

GCAGCTCGAAGTGCTGCGCGAGGCCTCGGCATTCG

TCTCGCACTGCGGCATGAACTCGACGATGGAGGCG

CTGTTCTTCGGGGTGCCGCTGGTCGGGGTGCCGCA

GCAGGCCGAGCAGCTGATCAACGCCGAACGCGCCG

CGGAGCTGGGCTTCGGCACGGTCCTCGCGCCGGAG

GAGCTGACCGCGGCGCGGCTGCGGGAGAGCGTGGA

AGCGGTCGCCGCCGACGAGCGGATCCGCGCGAACC

TCGACGAAATCAGTGCCAAGCTGCGGAAACGCCGC

GGCGCGGTGCTGGCGGCGGACGCGCTGCTGGCGCA

ACTGGACCGAGCGGCGGCGGACGCGCTGCCGGACT

GA.

F10 glycosyltransferase protein sequence

SEQ ID NO: 5

MGKHIAFVSIPAQGHVNPALPLVSELVARGHRVSY

ATAPARLDQVAAAGAEPVPAPFRLPLPPGDGKLLD

ARTVGLRFEEFYASVVEVFPRLVEHFAADRPDLFC

VDAMTPVGRMVAQKLGVPLAAMHPTHASNKEFSLR

ATVMGIEGALSDPASVEVVVRAVQEVGRKVRAFAE

ENGVDPDYDMFDYPADHNLVFIPREFQIKGETFDD

RFRFPGPTIVERPDAGHWQPAGKPLLYISLGTLFN

DNLKFYRSCLDAFGGTEWQVAMSVGAEVDLAALGP

VPGNIDVRPHFPQLEVLREASAFVSHCGMNSTMEA

LFFGVPLVGVPQQAEQLINAERAAELGFGTVLAPE

ELTAARLRESVEAVAADERIRANLDEISAKLRKRR

GAVLAADALLAQLDRAAADALPD.

GA6-003 glycosyltransferase protein sequence

SEQ ID NO: 6

MGKHIAFVSIPAQGHVNPALPLVSELVARGHRVSY

ATAPARLDQVAAAGAEPVPAPFRLPLPPGDGKLLD

ARTVGLRFEEFYESVVEVFPRLVEYFAADRPDLFC

VDAMTPVGRMVAQKLGVPLAAMHPTHASNKEFSLR

ATVMGIEGALSDPASVEVVVRAVQEVGRKVRAFAE

ENGVDPDYDMFDYPADHNLVFIPREFQIKGETFDD

RFRFPGPTIVERPDAGHWQPAGKPLLYISLGTLFN

DNLKFYRSCLDAFGGTEWQVAMSVGAEVDLAALGP

VPGNIDVRPHFPQLEVLREASAFVSHCGMNSTMEA

LFFGVPLVGVPQQAEQLINAERAAELGFGTVLAPE

-continued

ELTAARLRESVEAVAADERIRANLDEISAKLRKRR

GAVLAADALLAQLDRAAADALPD.

REFERENCES (1) CDC. Antibiotic Resistance Threats in the United States, 2019. Atlanta, GA: U.S. Department of Health and Human Services, CDC; 2019.

(2) Wencewicz, T. A. (2019) Crossroads of Antibiotic Resistance and Biosynthesis. J Mol Biol 431, 3370-3399

(3) Bolam, D. N., Roberts, S., Proctor, M. R., Turkenburg, J. P., Dodson, E. J., Martinez-Fleites, C., Yang, M., Davis, B. G., Davies, G. J., and Gilbert, H. J. (2007) The crystal structure of two macrolide glycosyltransferases provides a blueprint for host cell antibiotic immunity. Proceedings of the National Academy of Sciences of the United States of America (4) Zmudka, M. W., Thoden, J. B., and Holden, H. M. (2013) The structure of DesR from *Streptomyces venezuelae*, a β-glucosidase involved in macrolide activation. Protein Science 22, 883-892.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound having the structure:
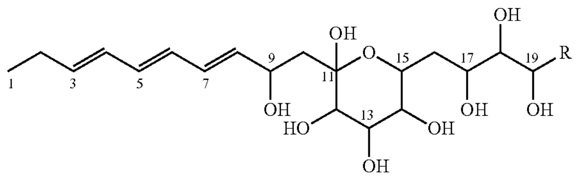
wherein R is selected from the group consisting of
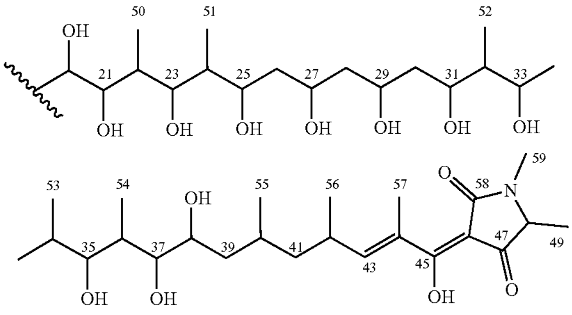
,
-continued
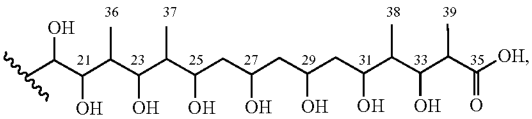
and
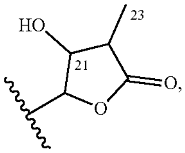
,
or a pharmaceutically acceptable salt thereof.
2. The compound or salt of claim 1, wherein the compound is:
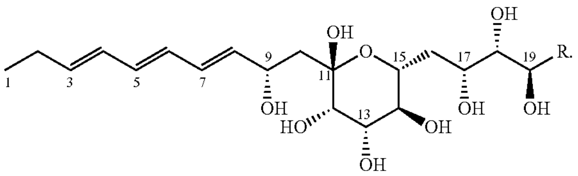
3. The compound or salt of claim 1, wherein R is:
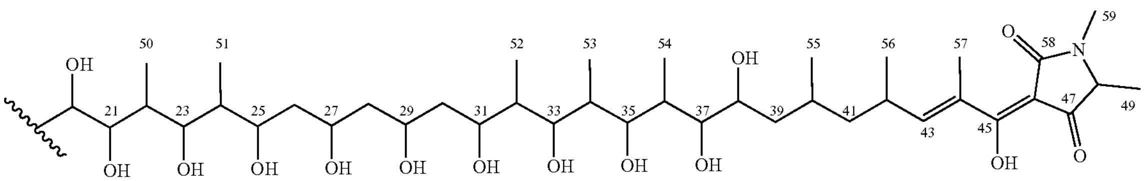
or
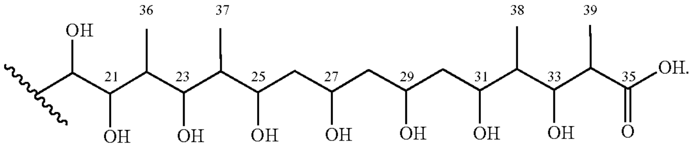
4. The compound or salt of claim 3, wherein R is:
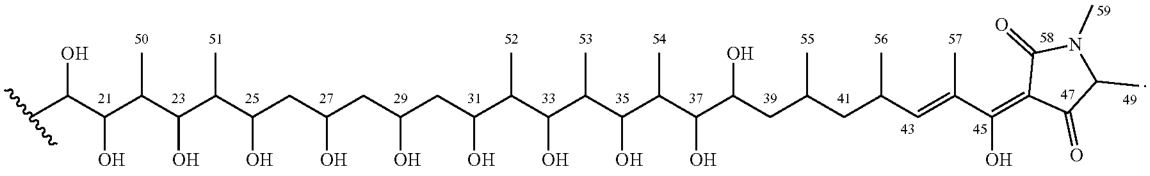 [SMILES: *C(O)C(O)C(C)C(O)C(C)C(O)CC(O)CC(O)CC(O)C(C)C(O)C(C)C(O)C(C)C(O)C(O)CC(C)CC(C)/C=C(C)/C(O)=C1/C(=O)C(C)N(C)C1=O]

5. A pharmaceutical composition comprising the compound or salt of claim 1 and a pharmaceutically acceptable carrier.

6. A pharmaceutical composition comprising the compound or salt of claim 4 and a pharmaceutically acceptable carrier.

7. A method for producing a compound or salt of claim 1 comprising culturing a microorganism that is *Amycolatopsis* strain F10 *Amycolatopsis* strain GA6-003 in a culture medium, thereby producing the compound or salt of claim 1 in an extracellular culture solution, separating the microorganism and the extracellular culture solution, and recovering the compound from the extracellular culture solution.

8. The method of claim 7, wherein the culture medium comprises sucrose, potassium sulfate, magnesium chloride, glucose, yeast extract, and casamino acid.

9. The method of claim 7, wherein the culture medium comprises yeast extract, beef extract, a peptone deried from casein, glucose, and agar.

10. The method of claim 7, wherein the microorganism comprises a 16S ribosomal DNA having SEQ ID NO:1.

11. A method of treating a subject having a bacterial infection or a fungal infection comprising administering to the subject an effective amount of a compound or salt of claim 1.

12. The method of claim 11, wherein the bacterial infection is caused by Gram-positive bacteria.

13. The method of claim 12, wherein the Gram-positive bacteria are selected from the group consisting of *S. aureus*, Methicillin-resistant *Staphylococcus aureus* (MRSA), *E. faecalis*, Vancomycin-resistant *E. faecalis*, and any combination thereof.

14. The method of claim 11, wherein fungal infection is caused by *C. albicans* or Amphotericin B-resistant *C. albicans*.

15. The method of claim 11, wherein the subject is a mammal.

16. The method of claim 15, wherein the mammal is a human.

17. The method of claim 11, wherein the compound is:

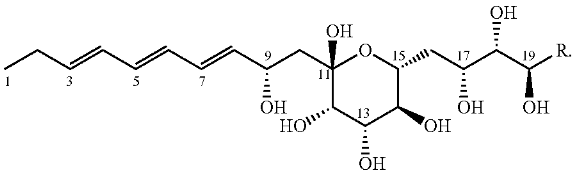

18. The method of claim 17, wherein R is:

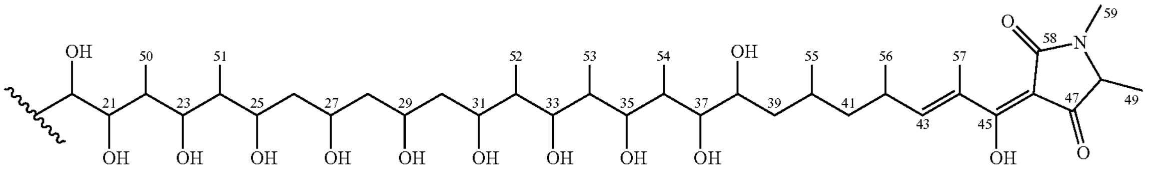

or

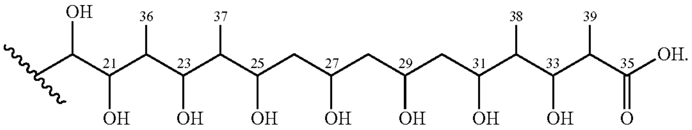

19. A compound having the structure:

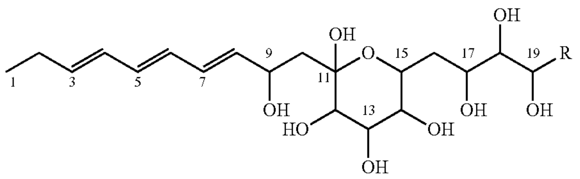

or a pharmaceutically acceptable salt thereof, wherein R is

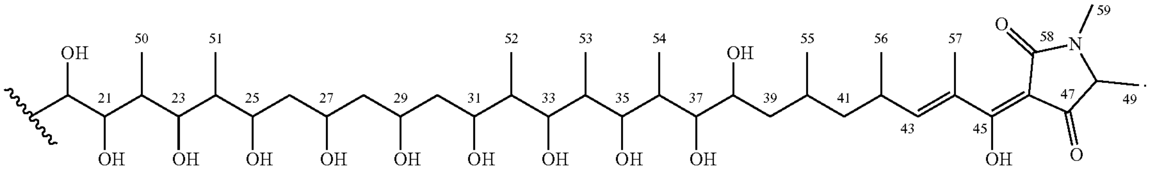 [SMILES: *C(O)C(O)C(C)C(O)C(C)C(O)CC(O)CC(O)CC(O)C(C)C(O)C(C)C(O)C(C)C(O)C(O)CC(C)CC(C)/C=C(C)/C(O)=C1/C(=O)C(C)N(C)C1=O]

20. A pharmaceutical composition comprising the compound or salt of claim 19 and a pharmaceutically acceptable carrier.

21. A method of treating a subject having a bacterial infection or a fungal infection comprising administering to the subject an effective amount of a compound or salt of claim 19.

* * * * *

SEQUENCE LISTING

<160> NUMBER OF SEQ ID NOS: 6

<210> SEQ ID NO 1
<211> LENGTH: 1392
<212> TYPE: DNA
<213> ORGANISM: Amycolatopsis sp.

<400> SEQUENCE: 1
gcagtcgaac gctgaaccgg tttcggccgg ggatgagtgg cgaacgggtg agtaacacgt 60
gggtaatctg ccctgtactc tgggataagc ctgggaaact gggtctaata ccggatacga 120
ccactgcagg catctgtggt ggtggaaagt tccggcggta tgggatgaac ccgcggccta 180
tcagcttgtt ggtggggtaa tggcctacca aggcgacgac gggtagccgg cctgagaggg 240
tgaccggcca cactgggact gagacacggc ccagactcct acgggaggca gcagtgggga 300
atattgcaca atgggcgcaa gcctgatgca gcgacgccgc gtgagggatg acggccttcg 360
ggttgtaaac ctctttcgcc agggacgaag cgagagtgac ggtacctgga taagaagcac 420
cggctaacta cgtgccagca gccgcggtaa tacgtagggt gcgagcgttg tccggaatta 480
ttgggcgtaa agagctcgta ggcggtttgt cgcgtcggcc gtgaaatctc cacgcttaac 540
gtggagcgtg cggtcgatac gggcagactt gagttcggca ggggagactg gaattcctgg 600
tgtagcggtg aaatgcgcag atatcaggag gaacaccggt ggcgaaggcg ggtctctggg 660
ccgatactga cgctgaggag cgaaagcgtg gggagcgaac aggattagat accctggtag 720
tccacgctgt aaacgttggg cgctaggtgt gggcgacatt ccacgttgtc cgtgccgtag 780
ctaacgcatt aagcgccccg cctggggagt acggccgcaa ggctaaaact caaaggaatt 840
gacgggggcc cgcacaagcg gcggagcatg tggattaatt cgatgcaacg cgaagaacct 900
tacctgggct tgacatgcgc cagacatccc cagagatggg gcttcccttg tggttggtgt 960
acaggtggtg catggctgtc gtcagctcgt gtcgtgagat gttgggttaa gtcccgcaac 1020
gagcgcaacc cttatcctac gttgccagcg cgtcatggcg gggactcgtg ggagactgcc 1080
ggggtcaact cggaggaagg tggggatgac gtcaagtcat catgcccctt atgtccaggg 1140
cttcacacat gctacaatgg ctggtacaga gggctgcgat accgcgaggt ggagcgaatc 1200
ccttaaagcc ggtctcagtt cggatcgcag tctgcaactc gactgcgtga agtcggagtc 1260
gctagtaatc gcagatcagc aacgctgcgg tgaatacgtt cccgggcctt gtacacaccg 1320
cccgtcacgt catgaaagtc ggtaacaccc gaagcccatg gcccaacccg caagggaggg 1380
agtggtcgaa gg 1392

<210> SEQ ID NO 2
<211> LENGTH: 1417
<212> TYPE: DNA
<213> ORGANISM: Amycolatopsis sp.

<400> SEQUENCE: 2
gacttcgtcc aatcgccagt cccaccttcg accactccct cccttgcggg ttgggccatg 60
ggcttcgggt gttaccgact ttcatgacgt gacgggcggt gtgtacaagg cccgggaacg 120
tattcaccgc agcgttgctg atctgcgatt actagcgact ccgacttcac gcagtcgagt 180
tgcagactgc gatccgaact gagaccggct ttaagggatt cgctccacct cgcggtatcg 240
cagccctctg taccagccat tgtagcatgt gtgaagccct ggacataagg ggcatgatga 300
cttgacgtca tccccacctt cctccgagtt gaccccggca gtctcccacg agtccccgcc 360
atgacgcgct ggcaacgtag gataagggtt gcgctcgttg cgggacttaa cccaacatct 420

-continued

```
cacgacacga gctgacgaca gccatgcacc acctgtacac caaccacaag ggaagcccca    480
tctctgggga tgtctggcgc atgtcaagcc caggtaaggt tcttcgcgtt gcatcgaatt    540
aatccacatg ctccgccgct tgtgcgggcc cccgtcaatt cctttgagtt ttagccttgc    600
ggccgtactc cccaggcggg gcgcttaatg cgttagctac ggcacggaca acgtggaatg    660
tcgcccacac ctagcgccca acgtttacag cgtggactac cagggtatct aatcctgttc    720
gctccccacg ctttcgctcc tcagcgtcag tatcggccca gagacccgcc ttcgccaccg    780
gtgttcctcc tgatatctgc gcatttcacc gctacaccag gaattccagt ctcccctgcc    840
gaactcaagt ctgcccgtat cgaccgcacg ctccacgtta agcgtggaga tttcacggcc    900
gacgcgacaa accgcctacg agctctttac gcccaataat tccggacaac gctcgcaccc    960
tacgtattac cgcggctgct ggcacgtagt tagccggtgc ttcttatcca ggtaccgtca   1020
ctctcgcttc gtccctggcg aaagaggttt acaacccgaa ggccgtcatc cctcacgcgg   1080
cgtcgctgca tcaggcttgc gcccattgtg caatattccc cactgctgcc tcccgtagga   1140
gtctgggccg tgtctcagtc ccagtgtggc cggtcaccct ctcaggccgg ctacccgtcg   1200
tcgccttggt aggccattac cccaccaaca agctgatagg ccgcgggttc atcccatacc   1260
gccggaactt tccacccccg aagatgcccc caaaggtcgt atccggtatt agacccagtt   1320
tcccaggctt atcccagagt acagggcaga ttacccacgt gttactcacc cgttcgccac   1380
tcatccccgg ccgaaaccgg ttcagcgttc gactgca                            1417
```

<210> SEQ ID NO 3
<211> LENGTH: 1227
<212> TYPE: DNA
<213> ORGANISM: Amycolatopsis sp.

<400> SEQUENCE: 3

```
atgggcaagc acatcgcttt cgtcagcatc ccggcgcagg gccacgtgaa tcccgcgctg     60
ccgctggtgt ccgagctggt cgcgcgcggg caccgggtca gctacgcgac cgcgccggcc    120
cggctcgacc aggtcgccgc ggcgggcgcg gagccggtgc cggctccgtt ccggctgccg    180
ctgccgcccg gggacggcaa actgctcgac gcccgcaccg tcggcctgcg gttcgaggag    240
ttctacgcat cggtcgtcga ggtcttcccc cggctggtgg agcatttcgc cgcggaccgg    300
cccgacctgt tctgcgtcga cgcgatgacg ccggtcggcc ggatggtcgc gcagaaactc    360
ggcgtcccgc tggccgccat gcatcccacc cacgccagca acaaggaatt ctcgctccgt    420
gccaccgtga tgggcatcga gggagcgctt tcggacccgg cttcggtcga ggtggtcgtc    480
cgcgccgtgc aggaggtggg ccgcaaggtc cgcgctttcg ccgaggaaaa cggggtcgac    540
cccgattacg acatgttcga ctatccggcc gaccacaacc tcgttttcat ccccagggaa    600
ttccagatca agggggagac tttcgacgac cggttccgtt tcccggggcc gacgatcgtc    660
gaacggcccg atgccgggca ttggcagccc gccgggaaac cgctgctgta catctcgctc    720
gggactttgt tcaacgacaa cctgaagttc taccgcagct gcctggacgc tttcggcggc    780
acggaatggc aggtggcgat gtcggtgggc gcggaggtcg acctcgcggc gctgggcccg    840
gtgccgggca acatcgacgt gcggccgcat ttcccgcagc tcgaagtgct gcgcgaggcc    900
tcggcattcg tctcgcactg cggcatgaac tcgacgatgg aggcgctgtt cttcggggtg    960
ccgctggtcg gggtgccgca gcaggccgag cagctgatca acgccgaacg cgccgcggag   1020
ctgggcttcg gcacggtcct cgcgccggag gagctgaccg cggcgcggct gcgggagagc   1080
```

-continued

```
gtggaagcgg tcgccgccga cgagcggatc cgcgcgaacc tcgacgaaat cagtgccaag   1140

ctgcggaaac gccggggcgc ggtgctggcg gcggacgcgc tgctggcgca actggaccga   1200

gcggcggcgg acgcgctgcc ggactga                                      1227


<210> SEQ ID NO 4
<211> LENGTH: 1227
<212> TYPE: DNA
<213> ORGANISM: Amycolatopsis sp.

<400> SEQUENCE: 4

atgggcaagc acatcgcttt cgtcagcatc ccggcgcagg gccacgtgaa tcccgcgctg     60

ccgctggtgt ccgagctggt cgcgcgcggg caccgggtca gctacgcgac cgcgccggcc    120

cggctcgacc aggtcgccgc ggcgggcgcg gagccggtgc cggctccgtt ccggctgccg    180

ctgccgcccg gggacggcaa actgctcgac gcccgcaccg tcggcctgcg gttcgaggag    240

ttctacgaat cggtcgtcga ggtcttcccc cggctggtgg agtatttcgc cgcggaccgg    300

cccgacctgt tctgcgtcga cgcgatgacg ccggtcggcc ggatggtcgc gcagaaactc    360

ggcgtcccgc tggccgccat gcatcccacc cacgccagca acaaggaatt ctcgctccgt    420

gccaccgtga tgggcatcga gggagcgctt tcggacccgg cttcggtcga ggtggtcgtc    480

cgcgccgtgc aggaggtggg ccgcaaggtc cgcgctttcg ccgaggaaaa cggggtcgac    540

cccgattacg acatgttcga ctatccggcc gaccacaacc tcgttttcat cccccgggaa    600

ttccagatca agggggagac tttcgacgac cggttccgtt tcccggggcc gacgatcgtc    660

gaacggcccg atgccgggca ttggcagccc gccgggaaac cgctgctgta catctcgctc    720

gggactttgt tcaacgacaa tctgaagttc taccgcagct gcctggacgc tttcggcggc    780

acggaatggc aggtggcgat gtcggtgggc gcggaggtcg acctcgcggc gctgggcccg    840

gtgccgggca acatcgacgt gcggccgcat ttcccgcagc tcgaagtgct gcgcgaggcc    900

tcggcattcg tctcgcactg cggcatgaac tcgacgatgg aggcgctgtt cttcggggtg    960

ccgctggtcg gggtgccgca gcaggccgag cagctgatca acgccgaacg cgccgcggag   1020

ctgggcttcg gcacggtcct cgcgccggag gagctgaccg cggcgcggct gcgggagagc   1080

gtggaagcgg tcgccgccga cgagcggatc cgcgcgaacc tcgacgaaat cagtgccaag   1140

ctgcggaaac gccgcggcgc ggtgctggcg gcggacgcgc tgctggcgca actggaccga   1200

gcggcggcgg acgcgctgcc ggactga                                      1227


<210> SEQ ID NO 5
<211> LENGTH: 408
<212> TYPE: PRT
<213> ORGANISM: Amycolatopsis sp.

<400> SEQUENCE: 5

Met Gly Lys His Ile Ala Phe Val Ser Ile Pro Ala Gln Gly His Val
1               5                   10                  15

Asn Pro Ala Leu Pro Leu Val Ser Glu Leu Val Ala Arg Gly His Arg
            20                  25                  30

Val Ser Tyr Ala Thr Ala Pro Ala Arg Leu Asp Gln Val Ala Ala Ala
        35                  40                  45

Gly Ala Glu Pro Val Pro Ala Pro Phe Arg Leu Pro Leu Pro Pro Gly
    50                  55                  60

Asp Gly Lys Leu Leu Asp Ala Arg Thr Val Gly Leu Arg Phe Glu Glu
65                  70                  75                  80
```

-continued

```
Phe Tyr Ala Ser Val Val Glu Val Phe Pro Arg Leu Val Glu His Phe
                85                  90                  95

Ala Ala Asp Arg Pro Asp Leu Phe Cys Val Asp Ala Met Thr Pro Val
            100                 105                 110

Gly Arg Met Val Ala Gln Lys Leu Gly Val Pro Leu Ala Ala Met His
        115                 120                 125

Pro Thr His Ala Ser Asn Lys Glu Phe Ser Leu Arg Ala Thr Val Met
    130                 135                 140

Gly Ile Glu Gly Ala Leu Ser Asp Pro Ala Ser Val Glu Val Val Val
145                 150                 155                 160

Arg Ala Val Gln Glu Val Gly Arg Lys Val Arg Ala Phe Ala Glu Glu
                165                 170                 175

Asn Gly Val Asp Pro Asp Tyr Asp Met Phe Asp Tyr Pro Ala Asp His
            180                 185                 190

Asn Leu Val Phe Ile Pro Arg Glu Phe Gln Ile Lys Gly Glu Thr Phe
        195                 200                 205

Asp Asp Arg Phe Arg Phe Pro Gly Pro Thr Ile Val Glu Arg Pro Asp
    210                 215                 220

Ala Gly His Trp Gln Pro Ala Gly Lys Pro Leu Leu Tyr Ile Ser Leu
225                 230                 235                 240

Gly Thr Leu Phe Asn Asp Asn Leu Lys Phe Tyr Arg Ser Cys Leu Asp
                245                 250                 255

Ala Phe Gly Gly Thr Glu Trp Gln Val Ala Met Ser Val Gly Ala Glu
            260                 265                 270

Val Asp Leu Ala Ala Leu Gly Pro Val Pro Gly Asn Ile Asp Val Arg
        275                 280                 285

Pro His Phe Pro Gln Leu Glu Val Leu Arg Glu Ala Ser Ala Phe Val
    290                 295                 300

Ser His Cys Gly Met Asn Ser Thr Met Glu Ala Leu Phe Phe Gly Val
305                 310                 315                 320

Pro Leu Val Gly Val Pro Gln Gln Ala Glu Gln Leu Ile Asn Ala Glu
                325                 330                 335

Arg Ala Ala Glu Leu Gly Phe Gly Thr Val Leu Ala Pro Glu Glu Leu
            340                 345                 350

Thr Ala Ala Arg Leu Arg Glu Ser Val Glu Ala Val Ala Ala Asp Glu
        355                 360                 365

Arg Ile Arg Ala Asn Leu Asp Glu Ile Ser Ala Lys Leu Arg Lys Arg
    370                 375                 380

Arg Gly Ala Val Leu Ala Ala Asp Ala Leu Leu Ala Gln Leu Asp Arg
385                 390                 395                 400

Ala Ala Ala Asp Ala Leu Pro Asp
                405


<210> SEQ ID NO 6
<211> LENGTH: 408
<212> TYPE: PRT
<213> ORGANISM: Amycolatopsis sp.

<400> SEQUENCE: 6

Met Gly Lys His Ile Ala Phe Val Ser Ile Pro Ala Gln Gly His Val
1               5                   10                  15

Asn Pro Ala Leu Pro Leu Val Ser Glu Leu Val Ala Arg Gly His Arg
            20                  25                  30

Val Ser Tyr Ala Thr Ala Pro Ala Arg Leu Asp Gln Val Ala Ala Ala
        35                  40                  45
```

```
Gly Ala Glu Pro Val Pro Ala Pro Phe Arg Leu Pro Leu Pro Pro Gly
    50                  55                  60

Asp Gly Lys Leu Leu Asp Ala Arg Thr Val Gly Leu Arg Phe Glu Glu
65                  70                  75                  80

Phe Tyr Glu Ser Val Val Glu Val Phe Pro Arg Leu Val Glu Tyr Phe
                85                  90                  95

Ala Ala Asp Arg Pro Asp Leu Phe Cys Val Asp Ala Met Thr Pro Val
            100                 105                 110

Gly Arg Met Val Ala Gln Lys Leu Gly Val Pro Leu Ala Ala Met His
        115                 120                 125

Pro Thr His Ala Ser Asn Lys Glu Phe Ser Leu Arg Ala Thr Val Met
    130                 135                 140

Gly Ile Glu Gly Ala Leu Ser Asp Pro Ala Ser Val Glu Val Val Val
145                 150                 155                 160

Arg Ala Val Gln Glu Val Gly Arg Lys Val Arg Ala Phe Ala Glu Glu
                165                 170                 175

Asn Gly Val Asp Pro Asp Tyr Asp Met Phe Asp Tyr Pro Ala Asp His
            180                 185                 190

Asn Leu Val Phe Ile Pro Arg Glu Phe Gln Ile Lys Gly Glu Thr Phe
        195                 200                 205

Asp Asp Arg Phe Arg Phe Pro Gly Pro Thr Ile Val Glu Arg Pro Asp
    210                 215                 220

Ala Gly His Trp Gln Pro Ala Gly Lys Pro Leu Leu Tyr Ile Ser Leu
225                 230                 235                 240

Gly Thr Leu Phe Asn Asp Asn Leu Lys Phe Tyr Arg Ser Cys Leu Asp
                245                 250                 255

Ala Phe Gly Gly Thr Glu Trp Gln Val Ala Met Ser Val Gly Ala Glu
            260                 265                 270

Val Asp Leu Ala Ala Leu Gly Pro Val Pro Gly Asn Ile Asp Val Arg
        275                 280                 285

Pro His Phe Pro Gln Leu Glu Val Leu Arg Glu Ala Ser Ala Phe Val
    290                 295                 300

Ser His Cys Gly Met Asn Ser Thr Met Glu Ala Leu Phe Phe Gly Val
305                 310                 315                 320

Pro Leu Val Gly Val Pro Gln Gln Ala Glu Gln Leu Ile Asn Ala Glu
                325                 330                 335

Arg Ala Ala Glu Leu Gly Phe Gly Thr Val Leu Ala Pro Glu Glu Leu
            340                 345                 350

Thr Ala Ala Arg Leu Arg Glu Ser Val Glu Ala Val Ala Ala Asp Glu
        355                 360                 365

Arg Ile Arg Ala Asn Leu Asp Glu Ile Ser Ala Lys Leu Arg Lys Arg
    370                 375                 380

Arg Gly Ala Val Leu Ala Ala Asp Ala Leu Leu Ala Gln Leu Asp Arg
385                 390                 395                 400

Ala Ala Ala Asp Ala Leu Pro Asp
                405
```